US008287587B2

(12) United States Patent
Moriuchi

(10) Patent No.: US 8,287,587 B2
(45) Date of Patent: Oct. 16, 2012

(54) SELF-EXPANDABLE STENT

(75) Inventor: Yousuke Moriuchi, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 502 days.

(21) Appl. No.: 12/492,843

(22) Filed: Jun. 26, 2009

(65) Prior Publication Data

US 2009/0319027 A1 Dec. 24, 2009

Related U.S. Application Data

(63) Continuation of application No. PCT/JP2007/075128, filed on Dec. 27, 2007.

(30) Foreign Application Priority Data

Dec. 28, 2006 (JP) ................................. 2006-354827

(51) Int. Cl.
A61F 2/06 (2006.01)
(52) U.S. Cl. ..................................... 623/1.15; 623/1.18
(58) Field of Classification Search .................. 606/108, 606/191, 194, 200; 623/1.11–1.54
See application file for complete search history.

(56) References Cited

U.S. PATENT DOCUMENTS

| 5,925,061 | A | 7/1999 | Ogi et al. |
| 6,171,334 | B1 | 1/2001 | Cox |
| 6,620,201 | B1 | 9/2003 | Nadal et al. |
| 7,618,445 | B2 * | 11/2009 | Moriuchi et al. ............ 623/1.15 |
| 2001/0056298 | A1 | 12/2001 | Brown et al. |
| 2002/0111669 | A1 | 8/2002 | Pazienza et al. |
| 2004/0093072 | A1 | 5/2004 | Pappas et al. |
| 2006/0253187 | A1 * | 11/2006 | Moriuchi et al. ............ 623/1.15 |

FOREIGN PATENT DOCUMENTS

EP 0 177 330 A2 4/1986

(Continued)

OTHER PUBLICATIONS

Form PCT/ISA/210 (International Search Report) dated Feb. 12, 2008.

(Continued)

Primary Examiner — Kathleen Sonnett
(74) Attorney, Agent, or Firm — Buchanan Ingersoll & Rooney PC

(57) ABSTRACT

A self-expandable stent includes axially arranged wavy-line annular bodies having a first shared linear portion and a second shared linear portion on one end side, a third shared linear portion and a fourth shared linear portion on the other end side, a first bent linear portion coupled with the first and third shared linear portions, a second bent linear portion coupled with the third and second shared linear portions, a third bent linear portion coupled with the second and fourth shared linear portions, and a fourth bent linear portion coupled with the fourth and first shared linear portions. Two of the four bent linear portions have a first equal number of bends and a common form at inversion, and the other two of the four bent linear portions have an equal number of bends different from the first equal number of bends and a common form at inversion.

13 Claims, 8 Drawing Sheets

FOREIGN PATENT DOCUMENTS

| | | |
|---|---|---|
| JP | 61-087540 A | 5/1986 |
| JP | 7-178124 A | 7/1995 |
| JP | 8-000738 A | 1/1996 |
| JP | 8-196642 A | 8/1996 |
| JP | 11-262531 A | 9/1999 |
| JP | 2001-137353 A | 5/2001 |
| JP | 2004-525729 A | 8/2004 |
| WO | WO 97/32546 A1 | 9/1997 |
| WO | WO 02/091958 A1 | 11/2002 |

OTHER PUBLICATIONS

International Preliminary Report on Patentability of Application No. PCT/JP2007/075128 dated Jul. 07, 2009.

Written Opinion of the International Searching Authority of Application No. PCT/JP2007/075128.

Official Action issued Dec. 6, 2011 by the Japanese Patent Office in corresponding Japanese Application No. 2006-354827, and a partial translation thereof.

* cited by examiner

SELF-EXPANDABLE STENT

This application is a continuation of International Application No. PCT/JP2007/075128 filed on Dec. 27, 2007, the entire content of which is incorporated herein by reference. This application also claims priority based on Japanese Application No. 2006-354827 filed on Dec. 28, 2006, the entire content of which is incorporated herein by reference.

TECHNICAL FIELD

The disclosure here relates to a self-expandable stent used for the medical care of a constricted part (constriction) or an obstructed portion (obstruction) in a lumens, such as a blood vessel, a biliary duct, a trachea, an esophagus, a urethra, and other organs.

BACKGROUND DISCUSSION

Stents are tubular medical devices which are indwelled in a lumen in order to expand a constricted part or an obstructed portion and secure the lumen in order to treat various diseases caused when blood vessels or other lumens in a living body are constricted or obstructed. Since the stent is inserted into the body from the outside of the body, the stent has a small diameter at the time of insertion, the stent is expanded or restored at a targeted constricted part or obstructed part to make its diameter larger, and a lumen is held in an enlarged state. Stents are sometimes classified as self-expandable stents and balloon expandable stents according to the function and expansion mode of the stent. The balloon expandable stent has no expansion function in the stent itself (i.e., no self-expanding function). After the stent is inserted into the targeted part, a balloon is located in the stent, the balloon is expanded, and the stent is expanded (plastically deformed) by the expansive force of the balloon and is brought into close contact with and fixed to the inner surface of the targeted lumen.

In the self-expandable stent, a number of shapes are suggested and are actually used for patients. The initial types of self-expandable stents included one, disclosed in Japanese Patent Publication No. 4-32662 obtained by bending a wire to utilize the repulsive force thereof, and another one described in Japanese Patent No. 2735795) obtained by knitting a wire into the shape of a blade. These stents had difficulties in fine working since the wires are bent, and the blade-shaped stent had a problem in that the length of the stent differs greatly before and after being indwelled in the body.

The present applicant has also suggested a stent as described in Japanese Application Publication No. 8-000738 in which a superelastic pipe is cut out and manufactured by a laser or the like. This technique enhances the working accuracy and enables the stent to form various shapes. However, in the basic structure of the stent, a plurality of wavy-line annular bodies is arranged in the axial direction, and adjacent wavy-line annular bodies are connected together by a connector.

Additionally, the stent disclosed in Japanese Application Publication No. 11-505441 is characterized in that a connector is connected diagonally.

Additionally, as another structural characteristic, the apexes of adjacent wavy-line annular bodies enter the adjacent wavy-line annular bodies. A stent of this type is the arrowhead type stent disclosed in JP-T-2000-506753. In JP-T-2002-518087, the apexes of wavy-line annular bodies are connected by a connector parallel to an axis. In Japanese application Publication No. 2001-137353, the apex with the apex of wavy-line annular bodies and the intermediate portion with the intermediate portion of wavy-line annular bodies are connected by a connector.

Additionally, there is a stent in which a wavy-line annular body which constitutes the stent is not an annular body but a spiral body, and the stent is constituted by one or a plurality of the spiral bodies from a front end of the stent to a rear end of the stent. An example of a stent of this type is one in which zigzag elements are connected together by a connector parallel to an axis in order to maintain the shape of a stent such as disclosed in JP-T-2001-509702. Additionally, as shown in Japanese Application Publication No. 8-196642, the present applicant has suggested a stent constituted by a plurality of spirals.

In many cases, the diameter after expansion of the self-expandable stent is 6 to 12 mm. The stent is housed in a tube called a sheath before expansion. The sheath generally has an external diameter of about 2 mm and an internal diameter of about 1.6 mm. For this reason, the stent is self-expanded from 3.75 times to 7.5 times on an external diameter basis when discharged from the sheath.

Additionally, in a stent for a coronary artery used widely as a balloon-expandable stent, the external diameter of about 1.2 mm is increased from about 2.5 mm to about 4 mm by the balloon. For this reason, this stent is expanded from 2.1 times to 3.3 times on an external diameter basis by the balloon.

As described above, since the self-expandable stent has a higher expansion ratio than the balloon expandable stent, the gap between elements after the expansion tends to increase. Many gaps are a factor which worsens the coverage, and may cause tissue growth between the gaps, which causes restenosis. Additionally, when the line width of each element is made small in order to improve coverage, the expansive force becomes weak, and thus, a certain line width is required.

In all the recent stents described above, a connector connects the respective wavy-line annular bodies together. The connector functions simply to connect the wavy-line annular bodies together.

The stent should also desirably be pliable in the axial direction. If the stent is hard in the axial direction, upon inserting the stent into a lumen, such as a bent blood vessel or biliary duct, there is a possibility that the stent may tend to straighten out the bend, and the tissue may be stimulated at the both ends of the stent and cause restenosis. An example of a stent of a type in which wavy-line annular bodies are independent and are connected together by a connector is the stent in Japanese application publication No. 11-262531. A stent such as this tends to be relatively hard in the axial direction.

Meanwhile, in a stent of a type where the apexes of wavy-line annular bodies are adjacent to each other between wavy-line annular bodies, for example the stent in JP-T-2002-518087, each element is long and apexes of adjacent elements are included.

SUMMARY

The self-expandable stent disclosed here has good coverage characteristics, exhibits an expansive radial force above a certain level, and is advantageously pliable in the axial direction.

The self-expandable stent includes a plurality of wavy-line annular bodies in the axial direction. Each wavy-line annular body has a plurality of one-end-side bends having apexes on one end side of the stent in the axial direction and a plurality of other-end-side bends having apexes on the other end side of the stent in the axial direction. The wavy-line annular bodies adjacent to each other on the other end side of the stent in the axial direction have at least two shared linear portions having a starting end at one apex or in its vicinity of the other-end-side bend in the wavy-line annular body on one end side of the stent in the axial direction and having a terminating end at a substantially intermediate portion between the apex of the other-end-side bend and the apex of the one-end-side bend, and the adjacent wavy-line annular bodies are integrated by the shared linear portions. Each wavy-line annular body of the stent other than at least those at one end and a base end has a first shared linear portion and a second shared linear portion located on one end side, a third shared linear portion and a fourth shared linear portion located on the other end side, a first bent linear portion having one end coupled with the first shared linear portion and the other end coupled with the third shared linear portion, a second bent linear portion having one end coupled with the third shared linear portion and the other end coupled with the second shared linear portion, a third bent linear portion having one end coupled with the second shared linear portion and the other end coupled with the fourth shared linear portion, and a fourth bent linear portion having one end coupled with the fourth shared linear portion and the other end coupled with the first shared linear portion. Two bent linear portions out of the first to fourth bent linear portions have the same number of bends and substantially the same form at the time of inversion, and the other two bent linear portions out of the first to fourth bent linear portions have the same number of bends which is different from the number of bends of the two bent linear portions and substantially the same form at the time of inversion.

DETAILED DESCRIPTION

Figure 1:
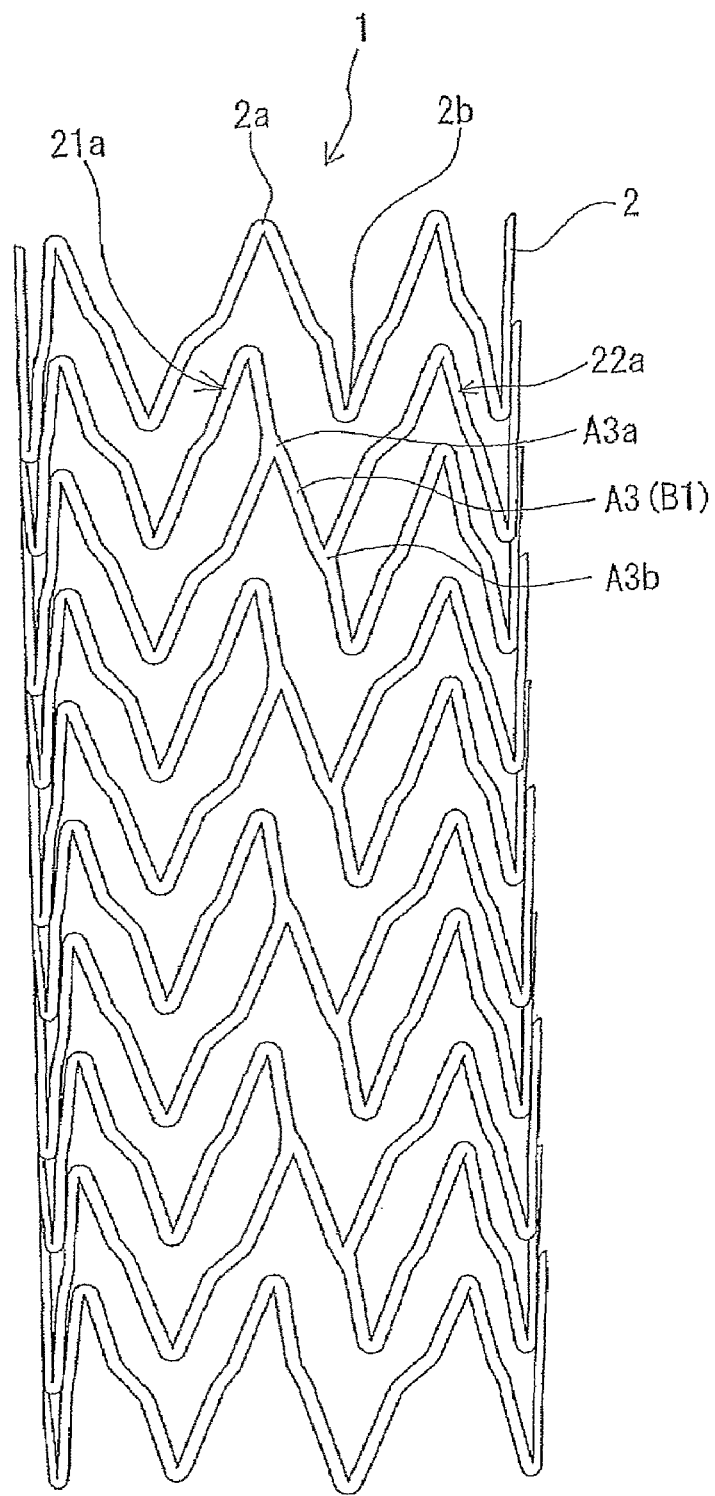
FIG. 1 is a front view of a self-expandable stent according to one embodiment disclosed here.

A self-expandable stent for indwelling in a living body according to one embodiment disclosed here is illustrated in FIGS. 1-4. The self-expandable stent 1 of the invention includes a plurality of adjacently positioned wavy-line annular bodies 2 arranged one after another in the axial or longitudinal direction of the stent. In the disclosed embodiments, each wavy-line annular body 2 has a plurality of one-end-side bends 2a forming apexes on one end side of the stent 1 in the axial direction and a plurality of other-end-side bends 2b forming apexes on the other (opposite) end side of the stent 1 in the axial direction. Generally speaking, axially adjacent wavy-line annular bodies 2 have at least two shared linear portions, both of which have a starting end at the apex formed by the other-end-side bend 2b of a first wavy-line annular body 2 on one end side of the stent 1 in the axial direction and a terminating end at an intermediate portion between such apex of the other-end-side bend 2b and the apex of the one-end-side bend 2a of an axially adjacent second wavy-line annular body 2. With reference to the illustrations in the drawing figures, the one end side refers to the upper end side (upper side), while the other end side refers to the lower end side (lower side). In other words, in FIG. 2 for example, the one end side of each wavy-line annular body 2 refers to the upper axial end side of the wavy-line annular body 2, and the other end side of each wavy-line annular body 2 refers to the lower axial end side of the wavy-line annular body 2.

Figure 2:
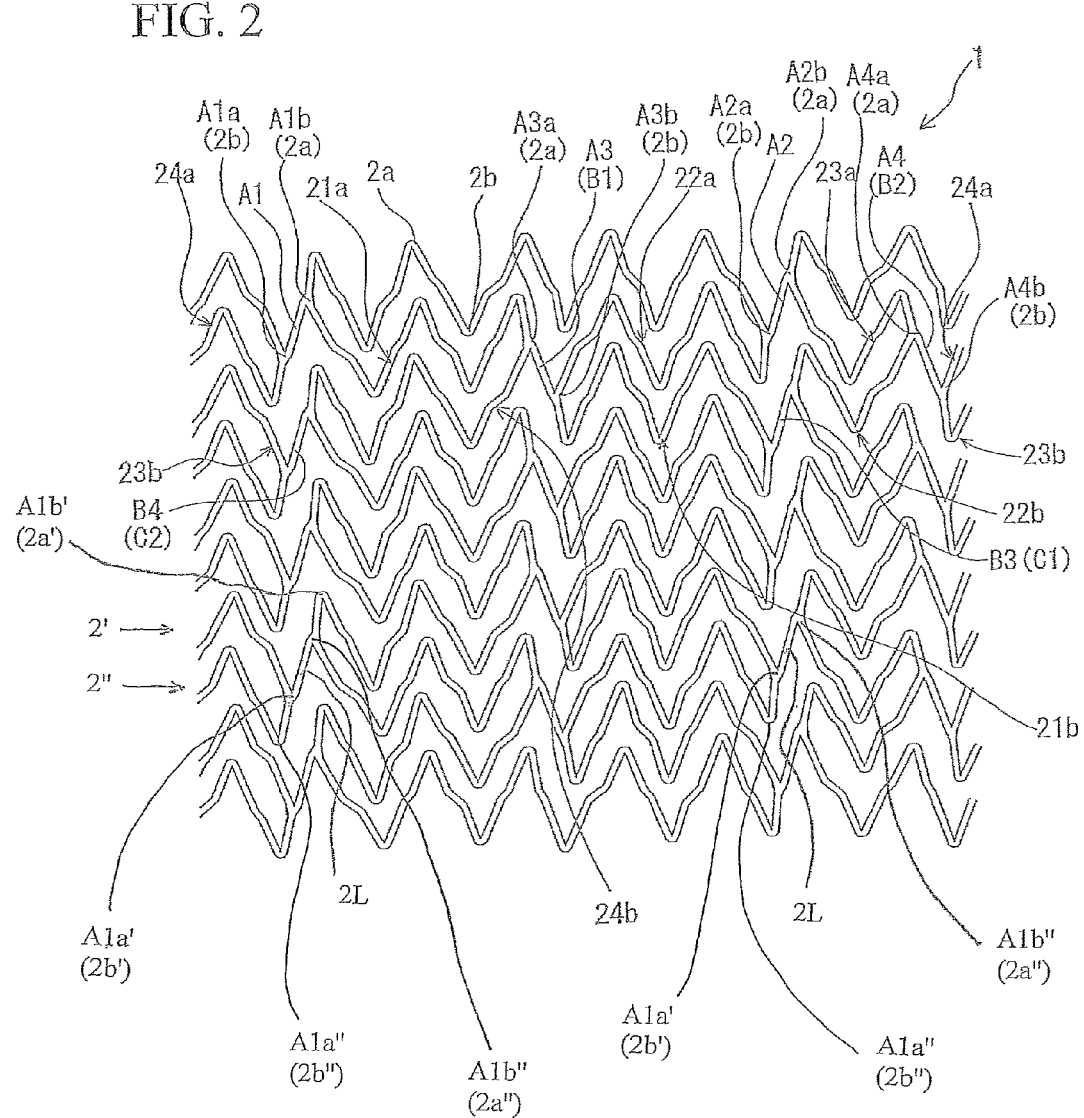
FIG. 2 is a development view of the stent shown in FIG. 1 (a plan view of the stent shown in FIG. 1 cut along the longitudinal extent of the stent and laid flat).

As an example, and with reference to FIG. 2, the wavy-line annular body 2' and the axially adjacent wavy-line annular body 2" have at least two shared linear portions 2L, 2L. Generally speaking, each shared linear portion 2L is an intermediate straight portion (inclusive of substantially straight portion in which the portion is not precisely straight (e.g., due to minor variations associated with manufacturing tolerances for instance) but nevertheless produces substantially the same result/function as a straight portion) located between the apex A1a" formed by the other-end-side bend 2b" of one wavy-line annular body 2" on the other end side of the stent 1 in the axial direction and the apex A1b' formed by the one-end-side bend 2a' of the wavy-line annular body 2' located axially adjacent on the one-end-side of the one wavy-line annular body 2" as shown in FIG. 2. More specifically, each of the shared linear portions 2L, 2L has one end at the apex A1a' formed by the other-end-side bend 2b' of first wavy-line annular body 2' and an opposite end at the apex A1b" formed by the one-end-side bend 2a" of a second wavy-line annular body 2" positioned axially adjacent, and on the other-end-side of, the first wavy-line annular body 2". Stated differently, each shared linear portion forms a part of one wavy-line annular body and also forms a part of the axially adjacent wavy-line annular body. The axially adjacent wavy-line annular bodies are integrated or connected to one another by the shared linear portions. In the illustrated embodiment, the axially adjacent wavy-line annular bodies are integrated or connected to one another exclusively by the shared linear portions.

In the illustrated embodiment, each wavy-line annular body 2 of the stent 1, other than the wavy-line annular body 2 at one axial end of the stent and the wavy-line annular body 2 at the opposite axial end (base end) of the stent, comprises: a first shared linear portion A1 and a second shared linear portion A2 located on one axial end side of the wavy-line annular body; a third shared linear portion A3 and a fourth shared linear portion A4 located on the opposite axial end side of the wavy-line annular body; a first bent linear portion (multi-bend portion) 21a having one end coupled with the first shared linear portion A1 and the other end coupled with the third shared linear portion A3, a second bent linear portion (multi-bend portion) 22a having one end coupled with the third shared linear portion A3 and the other end coupled with the second shared linear portion A2, a third bent linear portion (multi-bend portion) 23a having one end coupled with the second shared linear portion A2 and the other end coupled with the fourth shared linear portion A4, and a fourth bent linear portion (multi-bend portion) 24a having one end coupled with the fourth shared linear portion A4 and the other end coupled with the first shared linear portion A1.

Two of the bent linear portions out of the first to fourth bent linear portions have the same number of bends and the same form/configuration (inclusive of bent linear portions of substantially the same form/configuration that are not identical in form/configuration (e.g., due to variations associated with aspects of manufacturing) but nevertheless produce substantially the same result/function as bent linear portions identical in form/configuration) at the time of inversion. The expression "at the time of inversion" refers to the time when up and down, in other words, top and bottom, or in other words, one end and the other end (longitudinal) of the stent in the axial direction are inverted in a state where the bent linear portions are shown in the drawings.

Considered in more detail, and as shown in FIGS. 1-4, the illustrated embodiment of the self-expandable stent 1 for indwelling in a living body includes a plurality of wavy-line annular bodies 2 in the axial direction. Each wavy-line annular body 2 has a plurality of one-end-side bends comprising apexes 2a on one axial end side of the wavy-line annular body 2 and a plurality of other-end-side bends comprising apexes 2b on the other axial end side of the wavy-line annular body 2. The wavy-line annular bodies 2 adjacent to each other in the axial direction have a plurality of shared linear portions each having a starting end at one apex of the other-end-side bend 2b in one wavy-line annular body 2 and having a terminating end between such apex of the other-end-side bend 2b and the apex of the one-end-side bend 2a of the axially adjacent wavy-line annular body 2.

The stent of this embodiment is one which includes a plurality of axially arranged annular bodies in which the axially adjacent wavy-line annular bodies are integrated or connected by way of (and only by way of) shared linear portions that are partial shared portions of the respective wavy-line annular bodies. The stent does not possess a portion provided only as a so-called connecting portion. The shared portions integrating the axially adjacent wavy-line annular bodies all serve as portions which exhibit an expansive force.

Additionally, the stent of this embodiment is a stent, i.e., a so-called self-expandable stent, which is formed in a substantially cylindrical shape, is reduced in diameter upon insertion into a living body, and is able to be restored to the shape before the diameter reduction when indwelled in a living body. FIG. 1 shows the appearance configuration of the stent when the stent 1 is expanded.

The number of wavy-line annular bodies 2 forming the illustrated version of the stent 1 is 10 as in the drawing shown in FIG. 1. Although the number of axially adjacent wavy-line annular bodies 2 may differ depending on the length of the stent, the number is preferably 2 to 150, and particularly preferably 5 to 100.

Each wavy-line annular body 2 has a plurality of one-end-side bends comprising apexes on one axial end side and a plurality of other-end-side bends having apexes on the other axial end side. In addition, each wavy-line annular body 2 is an annularly continuous endless wavy-line body. Also, in the illustrated embodiment shown in FIG. 1, the wavy-line annular bodies 2 all possess the same configuration (inclusive of bodies 2 that are substantially the same in configuration in that they are not identical in configuration (e.g., due to variations associated with aspects of manufacturing) but nevertheless produce substantially the same result/function as wavy-line annular bodies identical in configuration). The one-end-side bends 2a and other-end-side bends 2b in the annular body 2 are formed alternately (i.e., in the circumferential direction of each wavy-line annular body, each one-end-side bend 2a is followed by one of the other-end-side bends 2b and each other-end-side bend 2a is followed by one of the one-end-side bends 2b), and each wavy-line annular body includes the same number of one-end-side bends 2a and other-end-side bends 2b. The number of one-end-side bends 2a in each wavy-line annular body is 8 in the illustrated embodiment and the number of other-end-side bends 2b in each wavy-line annular body is also 8. The number of one-end-side bends and the number of other-end-side bends is preferably 4 to 20 (each), more preferably 6 to 12. Additionally, the axial length of the wavy-line annular body 2 is preferably 1 to 10 mm, more preferably 1.5 to 5 mm.

The wavy-line annular bodies 2 adjacent to each other on the other end side of the stent 1 in the axial direction are integrated by the shared linear portions.

As described above, each wavy-line annular body 2 (for example, a second wavy-line annular body from one end of the stent 1 or a wavy-line annular body adjacent to a wavy-line annular body at one end in the axial direction) of the stent 1 other than perhaps those at one end and a base end includes: a first shared linear portion A1 and a second shared linear portion A2 on one axial end side, a third shared linear portion A3 and a fourth shared linear portion A4 on the other axial end side of the annular body, a first bent linear portion 21a having opposite ends coupled to the first and third shared linear portions A1, A3; a second bent linear portion 22a having opposite ends coupled with the third and second shared linear portions A3, A2; a third bent linear portion 23a having opposite ends coupled with the second and fourth shared linear portions A2, A4; and a fourth bent linear portion 24a having opposite ends coupled with the fourth and first shared linear portions A4, A1.

The first bent linear portion 21a and the second bent linear portion 22a, which are two bent linear portions out of the first to fourth bent linear portions, have the same number (four) of bends and the same form/configuration (inclusive of substantially the same as discussed above) at the time of inversion. In addition, although it is desirable that the first bent linear portion 21a and the second bent linear portion 22a have completely the same form/configuration at the time of inversion, they may be substantially same at the time of inversion.

Additionally, the third bent linear portion 23a and the fourth bent linear portion 24a which are the other two bent linear portions out of the first to fourth bent linear portions have the same number (two) of bends and the same form/configuration (inclusive of substantially the same as discussed above) at the time of inversion. The number of bends in the third and fourth bent linear portions 23a, 24a differs from the number of bends in the first and second bent linear portions 21a, 22a. In addition, although it is desirable that the third bent linear portion 23a and the fourth bent linear portion 24a have completely the same form at the time of inversion, they may be substantially same at the time of inversion.

The number of bends in each of the two bent linear portions with more bends is preferably about 4 to about 8, and the number of bends in each of the two bent linear portions with fewer bends is preferably about 2 to about 4. Particularly, the number of bends in each of the two bent linear portions with more bends is preferably 4, and the number of bends in each of the two bent linear portions with fewer bends is preferably 2.

Figure 4:
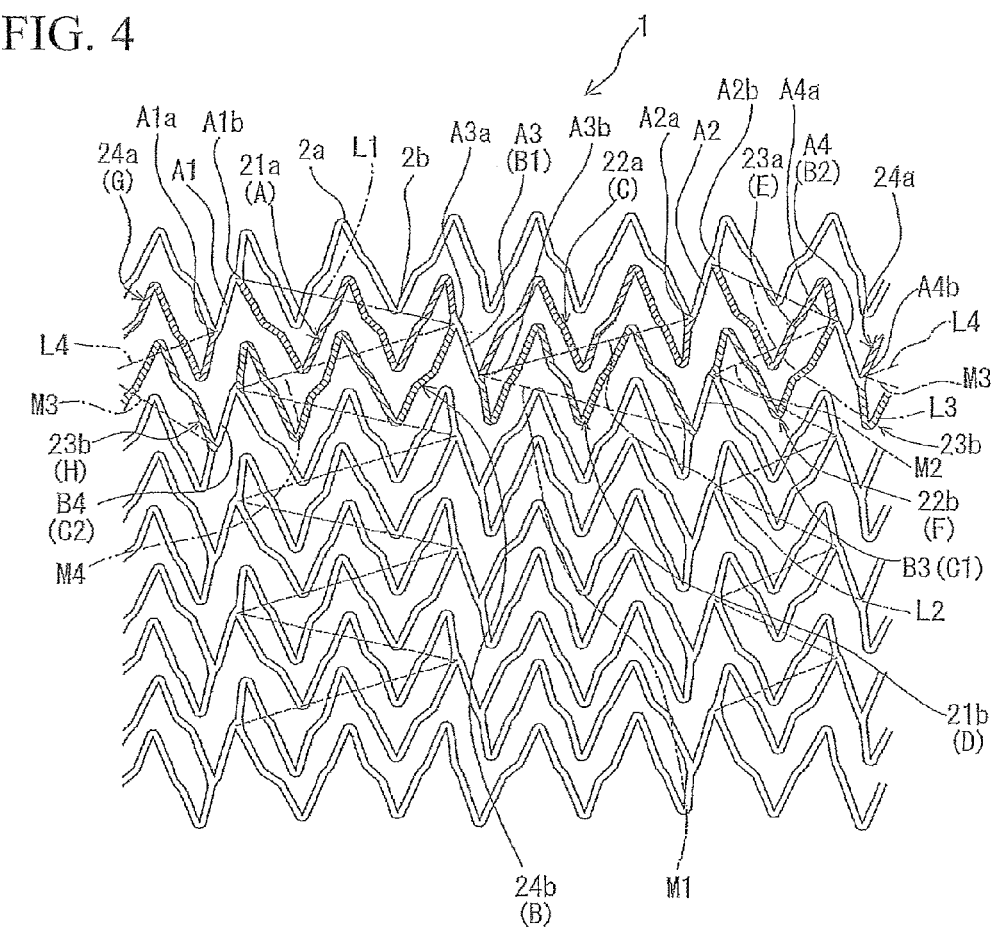
FIG. 4 is a development view similar to FIG. 2 serving as an explanatory view.

Additionally, in the stent 1 of this embodiment, as shown in FIG. 4, the two bent linear portions in one wavy-line annular body having the same number of bends are configured such that the directions or orientations of imaginary lines connecting one end and the other end of each bent linear portion are different from each other. Specifically, the direction/orientation of an imaginary line (a first imaginary line) L1 which connects one end and the other end of the first bent linear portion 21a, and the direction/orientation of an imaginary line (a second imaginary line) L2 which connects one end and the other end of the second bent linear portion 22a are in different directions (i.e., are not parallel). That is, L1 and L2 are not parallel. Particularly, as shown in FIG. 4, it is preferable that the direction/orientation of the first imaginary line L1 and the direction/orientation of the second imaginary line L2 are different from each other, but the inclination angle of each of the imaginary lines L1, L2 relative to the central axis of the stent is preferably the same (inclusive of inclination angles which, though not identical (e.g., due to manufacturing variations and/or tolerances) are nevertheless substantially the same and produce substantially the same result/function as identical inclination angles). Similarly, as shown in FIG. 4, the direction of an imaginary line (a third imaginary line) L3 which connects one end and the other end of the third bent linear portion 23a, and the direction of an imaginary line (a fourth imaginary line) L4 which connects one end and the other end of the fourth bent linear portion 24a extent in different directions (i.e., are not parallel). That is, L3 and L4 are not parallel. Particularly, as shown in FIG. 4, it is preferable that the direction/orientation of the third imaginary line L3 and the direction/orientation of the fourth imaginary line L4 be different from each other, but the inclination angle of each of the imaginary lines L3, L4 relative to the central axis of the stent is preferably the same (inclusive of inclination angles which, though not identical (e.g., due to manufacturing variations and/or tolerances) are nevertheless substantially the same and produce substantially the same result/ function as identical inclination angles)

A second wavy-line annular body from one end of the stent 1 is the above described first pattern wavy-line annular body.

As shown in FIGS. 2 and 4, a wavy-line annular body (a third wave-line annular body from one end of the stent 1) axially adjacent to the second wave-line annular body is a second pattern wavy-line annular body which will be described later.

The third wavy-line annular body from the one axial end side of the stent 1 has a first shared linear portion B1 and a second shared linear portion B2 which are located on one axial end side of the wavy-line annular body. The first shared linear portion B1 in the third wavy-line annular body is the same portion as the third shared linear portion A3 in the second wave-line annular body. Additionally, the second shared linear portion B2 in the third wavy-line annular body is the same portion as the fourth shared linear portion A4 in the second wave-line annular body. Also, the third wavy-line annular body from the one axial end side of the stent has a third shared linear portion B3 and a fourth shared linear portion B4 located on the other axial end side of the third wavy-line annular body. Moreover, the third wavy-line annular body from the one axial end side of the stent includes a first bent linear portion 21b having one end coupled to (connected to or integrated with) the first shared linear portion B1 and the other end coupled to (connected to or integrated with) the third shared linear portion B3, a second bent linear portion 22b having one end coupled to (connected to or integrated with) with the third shared linear portion B3 and the other end coupled to (connected to or integrated with) with the second shared linear portion B2, a third bent linear portion 23b having one end coupled to (connected to or integrated with) with the second shared linear portion B2 and the other end coupled to (connected to or integrated with) with the fourth shared linear portion B4, and a fourth bent linear portion 24b having one end coupled to (connected to or integrated with) with the fourth shared linear portion B4 and the other end coupled with the first shared linear portion B1.

The first bent linear portion 21b and the fourth bent linear portion 24b, which are two bent linear portions out of the first to fourth bent linear portions in the third wave-line annular body from one axial end side of the stent 1 have the same number (four) of bends and the same form (inclusive of substantially the same form as discussed above) at the time of inversion. In addition, although it is desirable that the first bent linear portion 21b and the fourth bent linear portion 24b have completely the same form at the time of inversion, they may be substantially same at the time of inversion.

Additionally, the second bent linear portion 22b and the third bent linear portion 23b which are two bent linear portions out of the first to fourth bent linear portions in the third wave-line annular body from one axial end side of the stent 1 have the same number (two) of bends and the same form (inclusive of substantially the same) at the time of inversion. The number of bends in the first and fourth bent linear portions 23b, 24b differs from the number of bends in the second and third bent linear portions 23a, 23d. In addition, although it is desirable that the third bent linear portion 23b and the second bent linear portion 22b have completely the same form at the time of inversion, they may be substantially same at the time of inversion.

In the stent 1 of this embodiment, as shown in FIG. 4, even in the third wavy-line annular body from one axial end side of the stent 1, the two bent linear portions having the same number of bends are configured such that the directions or orientations of imaginary lines which connect one end and the other end of each bent linear portion are different from each other. Specifically, the direction or orientation of an imaginary line (a first imaginary line) M1 which connects one end and the other end of the first bent linear portion 21b, and the direction or orientation of an imaginary line (a fourth imaginary line) M4 which connects one end and the other end of the fourth bent linear portion 24b are different. Particularly, as shown in FIG. 4, it is preferable that the direction or orientation of the first imaginary line M1 and the direction or orientation of the fourth imaginary line M4 be different from each other, but the inclination angle of each imaginary line relative to the central axis of the stent is the same (inclusive of substantially the same as discussed above). Similarly, the direction or orientation of an imaginary line (a third imaginary line) M3 which connects one end and the other end of the third bent linear portion 23b, and the direction or orientation of an imaginary line (a second imaginary line) M2 which connects one end and the other end of the second bent linear portion 22b are made to be different. Particularly, as shown in FIG. 4, it is preferable that the direction or orientation of the third imaginary line M3 and the direction or orientation of the second imaginary line M2 be different from each other, but the inclination angle of each imaginary line relative to the central axis of the stent is the same (inclusive of substantially the same as discussed above).

As shown in FIGS. 2 and 4, each even-numbered wave-line annular body from the one axial end side of the stent 1 is the above-mentioned first pattern wavy-line annular body, and each odd-numbered wave-line annular body from one end of the stent 1 is the above-mentioned second pattern wavy-line annular body.

In addition, each shared linear portion has one apex, which is one-end-side bend or the other-end-side bend in the wavy-line annular body 2 on one axial end side of the stent 1 in the axial direction, as a starting point, and has a terminating point between the apexes of one-end-side bend or the other-end-side bend continuous with this apex (may be starting end). For example, a shared linear portion can have a terminating end at the midpoint between the apexes of the one-end-side bend 2a which are continuous with the apex (also the starting end) of the bend 2b. In addition, although it is preferable that this terminating end be located at the midpoint, it may be located at a position which is anywhere between about 30/100 to about 49/100 of the total length between the apexes of the one-end-side bend 2a which are continuous with the apex (also the starting end of a shared linear portion) of the bend 2b. This total length refers to the length between the apex of the one-end-side-bend 2a and the apex of the other-end-side bend 2b. In addition, in such a case where the terminating end is not at the midpoint, it is preferable that the position of this terminating end be shifted toward the apex of the one-end-side bend 2a away from the midpoint.

The stent 1 having the configuration described above has a starting end branch formed by a starting end portion of a shared linear portion and a terminating end branch formed by a terminating end portion of the shared linear portion. Specifically, the starting end branch has a form whereby it branches into two heading toward one end with the starting end as the branch point, and the terminating end branch has a form whereby it branches into two heading toward the other end with the terminating end as the branch point.

Additionally, in the stent 1 of this embodiment, as shown in FIGS. 2 and 4, the arrangement form of each shared linear portion is substantially straight in the axial direction of the stent. Consequently, although the stent 1 has a complicated configuration as a whole, it includes a homogeneous expansive force and the ability to change shape. The stent 1 also includes four shared linear portion group rows which extend substantially parallel to the central axis of the stent 1. A first shared linear portion group row is constituted by a five shared linear portion group which is located on the left end side of FIGS. 2 and 4 and extends in the axial direction of the stent, a second shared linear portion group row is constituted by four shared linear portion groups which are located to the right (near the middle of FIGS. 2 and 4) of the above-mentioned first shared linear portion group row of FIGS. 2 and 4 and extends in the axial direction of the stent, a third shared linear portion group row is constituted by five shared linear portion groups which are located to the right side (on the right side from the middle of FIGS. 2 and 4) of the above-mentioned second shared linear portion group row of FIG. 2 and FIG. 4, and extends in the axial direction of the stent, and a fourth shared linear portion group row is constituted by four shared linear portion groups which are located on the right side (on the right end side of FIGS. 2 and 4) of the above-mentioned third shared linear portion group row of FIGS. 2 and 4 and extends in the axial direction of the stent.

Additionally, shared linear portions (for example, the first shared linear portion A1 and the second shared linear portion A2) located on one axial end side in one wavy-line annular body, and shared linear portions (for example, the third shared linear portion A3 and the fourth shared linear portion A4) located on the other axial end side extend in different directions with respect to the axis of the stent 1. It is preferable that the directions be different from each other, but the inclination angle of each of the shared linear portions relative to the central axis of the stent is preferably the same as discussed above.

Additionally, as shown in FIGS. 2 and 4, the apex portion of the one-end-side bends 2a of the wavy-line annular body 2 are each positioned in a space formed between the apexes of the other-end-side bends 2b of the axially adjacent wavy-line annular body, and an apex portion of each of the other-end-side bends 2b of the wavy-line annular body 2 is positioned in a space between the apexes of one-end-side bends 2a of another axially adjacent wavy-line annular body.

Figure 3:
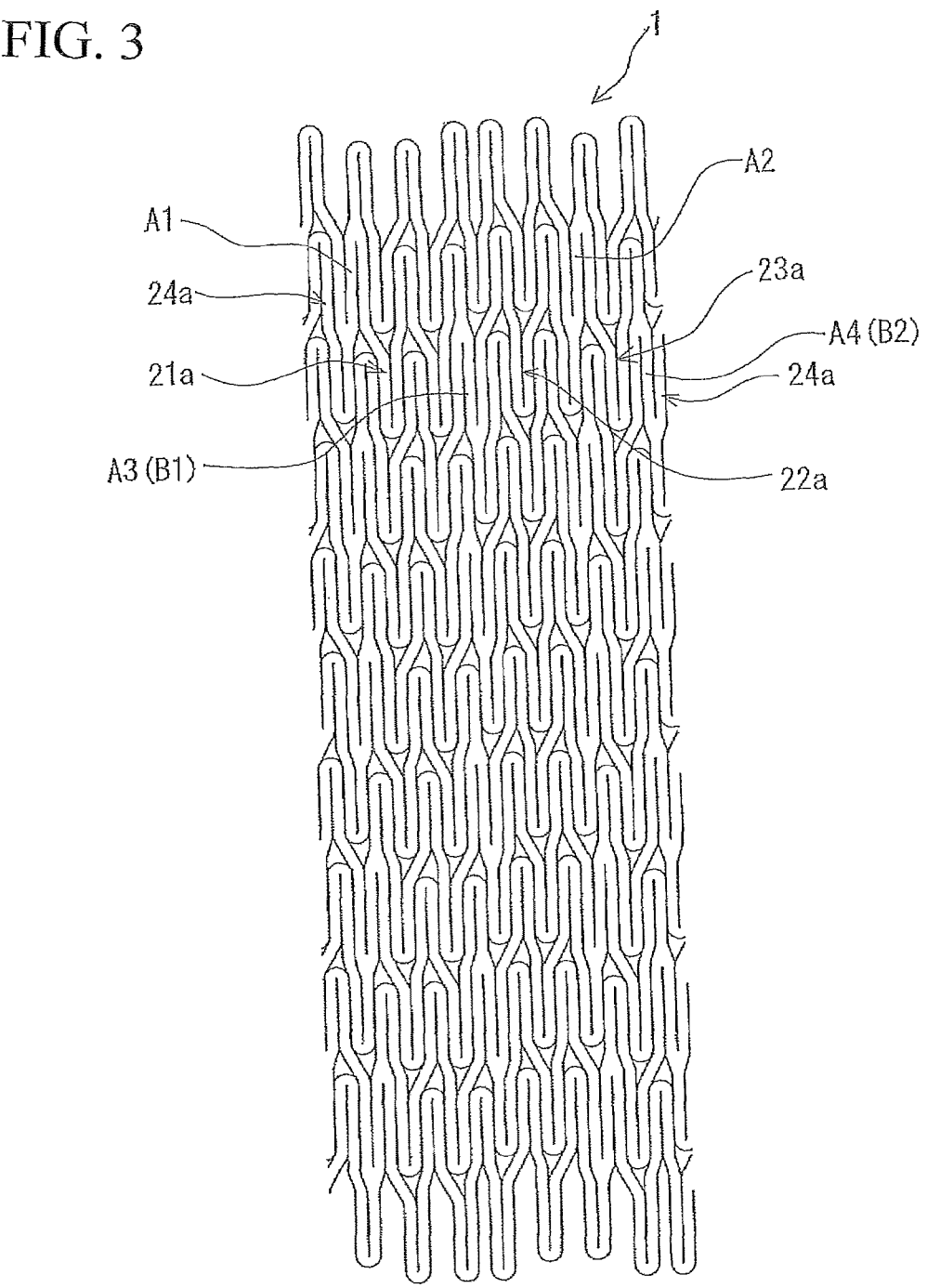
FIG. 3 is a development view of the stent shown in FIG. 1 in a state in which the diameter of the stent is reduced.

Moreover, in the stent 1 of this embodiment, in a contracted state shown in FIG. 3, there is almost no gap in the peripheral direction, and the respective elements are side by side. For this reason, the stent has relatively high coverage at the time of expansion.

Additionally, the stent 1 of this embodiment is as follows when described in more detail.

In this stent 1, as shown in FIG. 2, the wavy-line annular body 2 includes eight one-end-side apexes 2a, eight other-end-side apexes 2b, and sixteen substantially straight linear portions which connect them. Similarly, the wavy-line annular body axially adjacent to the wavy-line annular body 2 on the other end side in the axial direction includes eight one-end-side apexes 2a, eight other-end-side apexes 2b, and sixteen substantially straight linear portions which connect them. The above two wavy-line annular bodies 2 axially adjacent to each other are integrated by two common (shared) linear portions. Additionally, the above two wavy-line annular bodies 2 axially adjacent to each other are configured so as to overlap each other by about ½ of the axial length of one wavy-line annular body (in other words, so as to shift toward the other end). For this reason, each one-end-side apex 2a of a wavy-line annular body on the other end side relative to an axially adjacent wavy-line annular body on the one end side is positioned so that it enters a space between the other-end-side apexes of the axially adjacent wavy-line annular body on the one end side. The first shared linear portion A1 is a substantially straight portion which couples the other-end-side apex 2b (A1a) of the wavy-line annular body 2 on one end side with the one-end-side apex 2a (A1b) of the wavy-line annular body 2 on the other end side. Additionally, the second shared linear portion A2 is a substantially straight portion which couples the other-end-side apex 2b (A2a) of one wavy-line annular body 2 on one end side with the one-end-side apex 2a (A2b) of an axially adjacent wavy-line annular body 2 on the other end side. An apex shared by the shared linear portion is not an apex serving as a free end of one of the wavy-line annular bodies 2, and constitutes a branch. Similarly, the wavy-line annular body 2 adjacent to the above wavy-line annular body on the other end side in the axial direction is also integrated by having two common linear portions. These two wavy-line annular bodies 2 adjacent to each other are also configured so as to overlap each other by about ½ of the axial length of one wavy-line annular body (in other words, so as to shift toward the other end). For this reason, one-end-side apex 2a of a wavy-line annular body on the other end side is in the state of having entered into a space between the other-end-side apexes of a wavy-line annular body on one end side. The first shared linear portion B1 (A3) is a substantially straight portion which couples the other-end-side apex 2b (A3b) of the wavy-line annular body 2 on one end side with the one-end-side apex 2a (A3a) of the wavy-line annular body 2 on the other end side. Additionally, the second shared linear portion B2 (A4) is also a substantially straight portion which couples the other-end-side apex 2b (A4b) of the wavy-line annular body 2 on one end side with the one-end-side apex 2a (A4a) of the wavy-line annular body 2 on the other end side. An apex shared by the shared linear portion is not the apex serving as a free end, and constitutes a branch.

As shown in FIG. 2, there are the following features when the structure, other than the common linear portions in the stent 1, is observed. In a wavy-line annular body, the first bent linear portion 21a which has the terminating end A1b (midpoint) of the first shared linear portion A1 as a starting point extends diagonally toward the other end (upward in FIG. 2) and is bent at the first other-end-side apex 2b, extends diagonally toward one the one end (upward in FIG. 2) and is bent at the first one-end-side apex 2a, extends again diagonally toward the other end (downward in FIG. 2) and is bent at the second other-end-side apexes 2b, extends again diagonally toward one end (upward in FIG. 2) and is bent at the second one-end-side apex 2a, and has the midpoint A3a (also the starting point of the third shared linear portion A3) between the second one-end-side apex and the next other-end-side apex as a terminating point.

Additionally, the second bent linear portion 22a which has the terminating end A3b (midpoint) of the third shared linear portion A3 as a starting point extends diagonally toward one end (upward in FIG. 2) and is bent at the first one-end-side apex 2a, extends diagonally toward the other end (downward in FIG. 2) and is bent at the first other-end-side apex 2b, extends again diagonally toward one end (upward in FIG. 2) and is bent at the second one-end-side apex 2a, extends again diagonally toward the other end (downward in FIG. 2) and is bent at the second other-end-side apex 2b, and has the midpoint A2a (also the starting point of the second shared linear portion A2) between this second other-end-side apex and the next one-end-side apex as a terminating point.

Additionally, in a wavy-line annular body, the third bent linear portion 23a having the terminating end A2b (midpoint) of the second shared linear portion A2 as a starting point extends diagonally toward the other end (downward in FIG. 2) and is bent at the first other-end-side apex 2b, extends diagonally toward one end (upward in FIG. 2) and is bent at the first one-end-side apex 2a, and has the midpoint A4a (also the starting point of the fourth shared linear portion A4) between the first one-end-side apex and the next other-end-side apex as a terminating point. Additionally, the fourth bent linear portion 24a having the terminating end A4b (midpoint) of the fourth shared linear portion A4 as a starting point extends diagonally toward one end (upward in FIG. 2) and is bent at the first one-end-side apex 2a, extends diagonally toward the other end (downward in FIG. 2) and is bent at the first other-end-side apex 2b, and has the midpoint A1a (also the starting point of the first shared linear portion A1) between the first other-end-side apex and the next one-end-side apex as a terminating point.

Consequently, in all the first to fourth bent linear portions 21a, 22a, 23a, and 24a, both the starting point and the terminating point are located not at the apexes of bends of a linear body but at an intermediate portion of a substantially straight portion connecting the apexes of the bends.

Additionally, the first shared linear portion A1 and third shared linear portion A3 which are connected together by the first bent linear portion 21a face different directions or are oriented in different directions with respect to the central axis of the stent. Similarly, the second shared linear portion A2 and fourth shared linear portion A4 which are connected together by the third bent linear portion 23a face different directions or are oriented in different directions with respect to the central axis of the stent. Additionally, the first shared linear portion A1 and second shared linear portion A2 are inclined in the same direction with respect to the central axis of the stent. The third shared linear portion A3 and fourth shared linear portion A4 are inclined in the same direction with respect to the central axis of the stent.

Moreover, in the stent 1 of this embodiment, bent linear portions having the same number of bends in the axial direction of the stent are arranged in series so they axially line up with one another. Specifically, as shown in FIG. 4, in the stent 1, as for the wavy-line annular bodies excluding those at one axial end and the other axial end, a plurality of bent linear portions [21a: pattern A; (A) in the drawing] of the same pattern having four bends are arranged to alternate in a series, bent linear portions [24b: pattern B; (B) in the drawing] having four bends and a pattern different from the above bent linear portions (21a: pattern A) are arranged to alternate in a series, and the bent linear portions of two patterns (pattern A and pattern B) are arranged so as to alternate with each other.

The bent linear portions (pattern B) have a form in which the bent linear portions (pattern A) are horizontally inverted. An imaginary line, which connects one end and the other end of a bend of each of the bent linear portions (patterns A and B) which are arranged substantially in series in the axial direction of the stent, has almost the same length and a continuous zigzagging shape. The horizontal inversion, as described above and as will be described below, shows the state of being inverted laterally in the axial direction of a stent (in other words, a direction orthogonal to the axis).

Moreover, in the stent 1, as for the wavy-line annular bodies excluding those at one end and the other end, a plurality of bent linear portions [22a: pattern C; (C) in the drawing] of the same pattern having four bends are arranged to alternate in a series, bent linear portions [21b: pattern D; (D) in the drawing] having four bends and having a pattern different from the above bent linear portions are arranged to alternate in a series, and the bent linear portions of two patterns (pattern C and pattern D) are arranged so as to alternate with each other. The bent linear portions (pattern D) have a form in which the bent linear portions (pattern C) are inverted horizontally. Additionally, the bent linear portions (pattern C) have a form in which the bent linear portions (pattern A) are vertically inverted (in other words, up and down in the axial direction). An imaginary line, which connects one end and the other end of a bend of each of the bent linear portions (patterns C and D) which are arranged substantially in series in the axial direction of the stent, has almost the same length, and a continuous zigzagging shape.

Moreover, in the stent 1, as shown in FIG. 4, as for the wavy-line annular bodies excluding those at one end and the other end, a plurality of bent linear portions [23a: pattern E; (E) in the drawing] of the same pattern having two bends are arranged to alternate in a series, bent linear portions [22b: pattern F; (F) in the drawing] having two bends and a pattern different from the above bent linear portions are arranged to alternate in a series, and the bent linear portions of two patterns (pattern E and pattern F) are arranged so as to alternate with each other. The bent linear portions (pattern F) have a form in which the bent linear portions (pattern E) are horizontally inverted. An imaginary line, which connects one end and the other end of a bend of each of the bent linear portions (patterns E and F) which are arranged substantially in series in the axial direction of the stent, has almost the same length and a continuous zigzagging shape.

Moreover, in the stent 1, as for the wavy-line annular bodies excluding those at one end and the other end, a plurality of bent linear portions [24a: pattern G; (G) in the drawing] of the same pattern having two bends are arranged to alternate in a series, bent linear portions [23b: pattern H; (H) in the drawing] having two bends and having a pattern different from the above bent linear portions are arranged to alternate in a series, and the bent linear portions of two patterns (pattern G and pattern H) are arranged so as to alternate with each other. The bent linear portions (pattern H) have a form in which the bent linear portions (pattern G) are horizontally inverted. Additionally, the bent linear portions (pattern G) have a form in which the bent linear portions (pattern E) are vertically inverted (in other words, up and down in the axial direction). An imaginary line, which connects one end and the other end of a bend of each of the bent linear portions (patterns G and H) which are arranged substantially in series in the axial direction of the stent, has almost the same length and a continuous zigzagging shape.

In the stent of this embodiment, a continuous imaginary line, obtained by making a continuous imaginary line which connects one end and the other end of each bent linear portion of the bent linear portions located substantially in series in the axial direction of the stent, is in the shape of a zigzag having apexes which project in the peripheral direction of the stent. Additionally, in this stent 1, the zigzagging continuous imaginary line has a plurality of apexes which project by almost the same length in the peripheral direction of the stent.

Additionally, the stent may be a stent 10 of a pattern as shown in FIGS. 5 to 8.

FIGS. 5-8 illustrate another embodiment of the self-expandable stent for indwelling in a living body.

The self-expandable stent 10 of this embodiment and the above-described stent 1 have slight differences in the pattern of bent linear portions. Differences include the arrangement position of shared linear portions, though both are the same in their basic configurations.

The stent 10 of this second embodiment includes a plurality of axially arranged wavy-line annular bodies 2. Each wavy-line annular body 2 has a plurality of one-end-side bends 2a having apexes on one end side of the stent 10 in the axial direction and a plurality of other-end-side bends 2b having apexes on the other end side of the stent 10 in the axial direction. Like the embodiment described above, the wavy-line annular bodies 2 axially adjacent to each other on the other end side of the stent 10 in the axial direction have at least two shared linear portions each having a starting end at one apex of the other-end-side bend 2b in the wavy-line annular body 2 on one end side of the stent 10 in the axial direction and having a terminating end at a substantially intermediate portion between the apex of the other-end-side bend 2b and the apex of the one-end-side bend 2a (an intermediate portion of a substantially straight portion connecting apexes of two bends), and the adjacent wavy-line annular bodies are integrated by the shared linear portions.

The wavy-line annular bodies 2 axially adjacent to each other on the other end side of the stent 10 in the axial direction are integrated by shared linear portions in a manner similar to the stent 1 described above.

Figure 5:
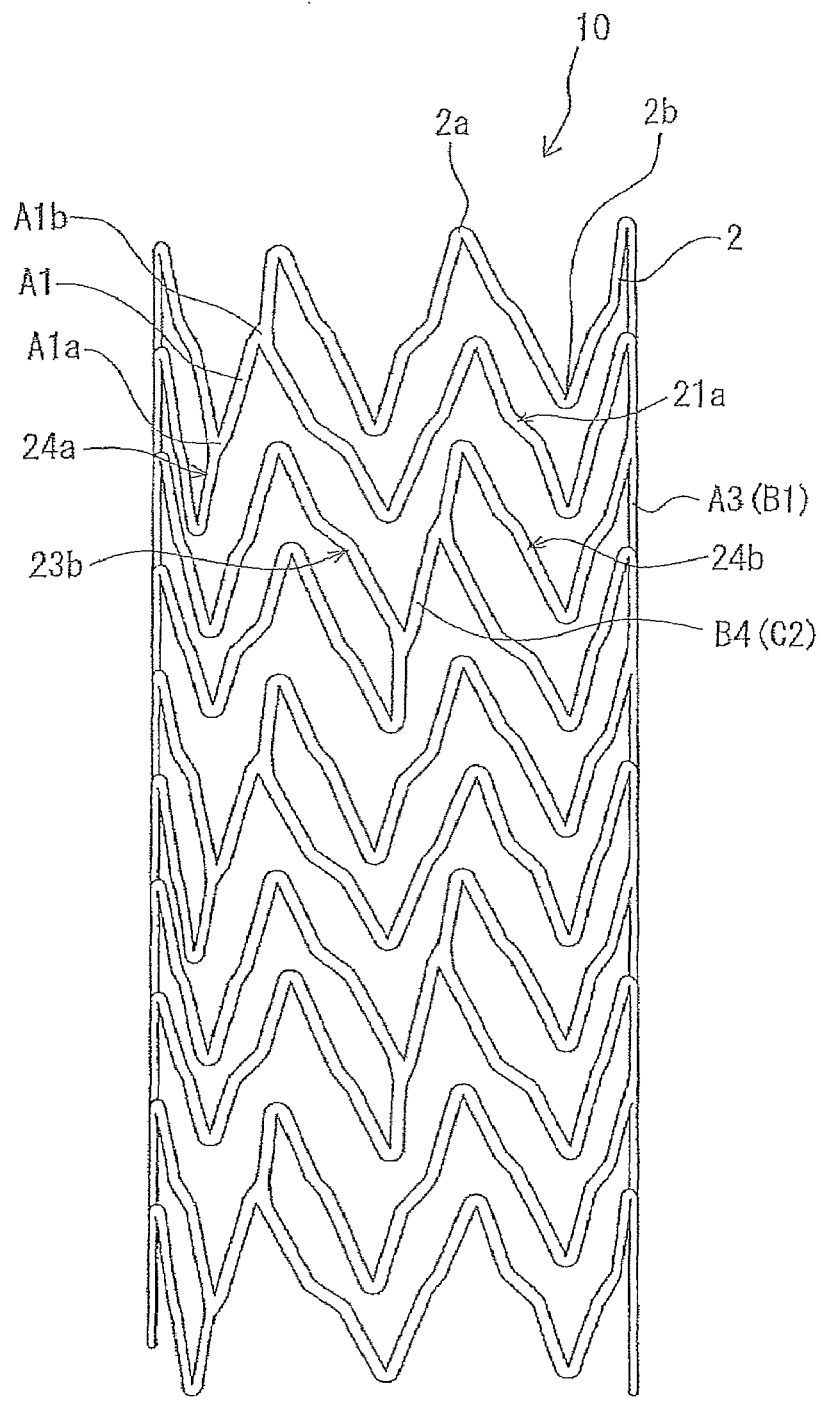
FIG. 5 is a front view of a self-expandable stent according to another embodiment disclosed here.
Figure 6:
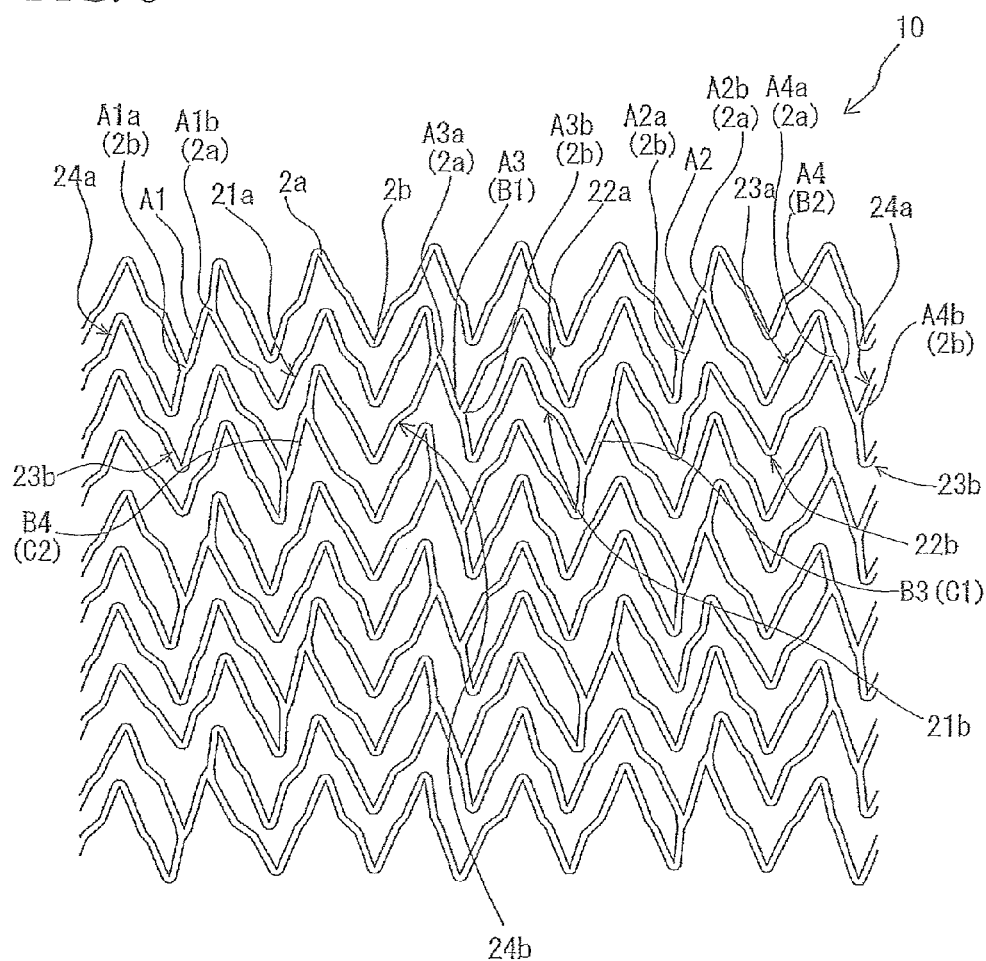
FIG. 6 is a development view of the stent shown in FIG. 5.
Figure 8:
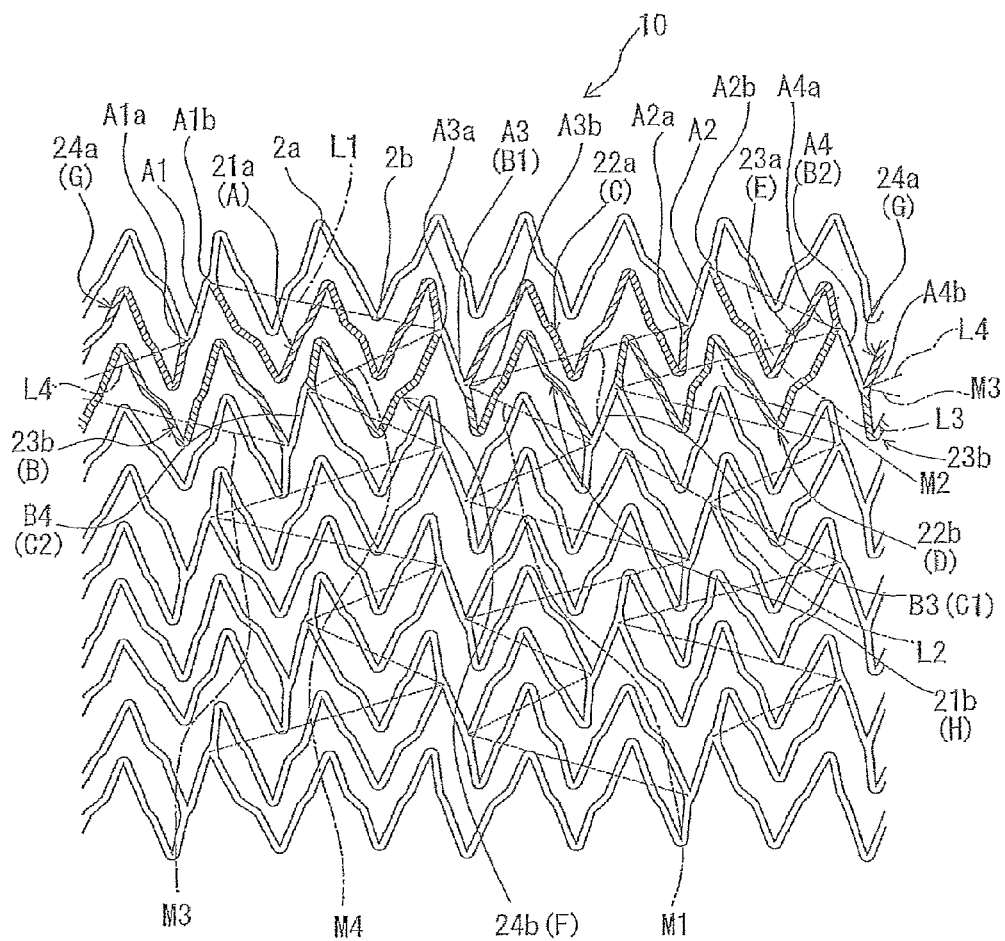
FIG. 8 is a development view similar to FIG. 6 serving as an explanatory view.

As shown in FIGS. 5, 6 and 8, each wavy-line annular body 2 of the stent 10 other than those at one end and a base end, specifically, a second wavy-line annular body from one end of the stent 10 (a wavy-line annular body adjacent to the wavy-line annular body at one end in the axial direction) has a first shared linear portion A1 and a second shared linear portion A2 located on one end side, a third shared linear portion A3 and a fourth shared linear portion A4 located on the other end side, a first bent linear portion 21a having one end coupled with the first shared linear portion A1 and the other end coupled with the third shared linear portion A3, a second bent linear portion 22a having one end coupled with the third shared linear portion A3 and the other end coupled with the second shared linear portion A2, a third bent linear portion 23a having one end coupled with the second shared linear portion A2 and the other end coupled with the fourth shared linear portion A4, and a fourth bent linear portion 24a having one end coupled with the fourth shared linear portion A4 and the other end coupled with the first shared linear portion A1.

The first bent linear portion 21a and the second bent linear portion 22a (constituting two bent linear portions out of the first to fourth bent linear portions) are formed to have the same number of bends (specifically four) and the same form/configuration at the time of inversion (inclusive of substantially the same form/configuration as described above). In addition, although it is desirable that the first bent linear portion 21a and the second bent linear portion 22a have completely the same form/configuration at the time of inversion, they may have simply the same pattern as described above.

Additionally, the third bent linear portion 23a and the fourth bent linear portion 24a (which constitute two other bent linear portions out of the first to fourth bent linear portions) are configured to have the same number (specifically two) of bends which is different from the number of bends of the above-mentioned two bent linear portions and the same form/configuration at the time of inversion (inclusive of substantially the same form/configuration as described above). In addition, although it is desirable that the third bent linear portion 23a and the fourth bent linear portion 24a have completely the same form at the time of inversion, they may have simply the same pattern as mentioned above.

Even in the stent 10 of this embodiment, as shown in FIG. 8 plan view of the stent, two bent linear portions having the same number of bends in one wavy-line annular body are configured such that the directions of imaginary lines which connect one end and the other end of each bent linear portion are different from each other. Specifically, the direction of an imaginary line (a first imaginary line) L1 which connects one end and the other end of the first bent linear portion 21a, and the direction of an imaginary line (a second imaginary line) L2 which connects one end and the other end of the second bent linear portion 22a are different. Particularly, as shown in FIG. 8, it is preferable that the direction of the first imaginary line L1 and the direction of the second imaginary line L2 be different from each other so they are not parallel, but the inclination angles of the imaginary lines relative to the central axis of the stent are the same (inclusive of substantially the same as described above). Similarly, the direction of an imaginary line (a third imaginary line) L3 which connects one end and the other end of the third bent linear portion 23a, and the direction of an imaginary line (a fourth imaginary line) L4 which connects one end and the other end of the fourth bent linear portion 24a are different. Particularly, as shown in FIG. 8, it is preferable that the direction of the third imaginary line L3 and the direction of the fourth imaginary line L4 be different from each other so they are not parallel, but the inclination angles of the imaginary lines relative to the central axis of the stent is the same (inclusive of substantially the same).

The second wavy-line annular body from one end of the stent 10 is the above-described first pattern wavy-line annular body.

As shown in FIGS. 6 and 8, a wavy-line annular body (a third wave-line annular body from one end of the stent 10) axially adjacent to the second wave-line annular body in the axial direction from one end of the stent 10 becomes a second pattern wavy-line annular body which will be described later.

The third wavy-line annular body from one end of the stent 10 has a first shared linear portion B1 and a second shared linear portion B2 which are located on one end side. The first shared linear portion B1 is the same portion as a third shared linear portion A3 in the second wave-line annular body from one end of the stent 1 described above. Additionally, the second shared linear portion B2 is the same portion as a fourth shared linear portion A4 in the second wave-line annular body from one end of the stent 10 described above. Moreover, this wavy-line annular body has a third shared linear portion B3 and a fourth shared linear portion B4 located on the other end side, a first bent linear portion 21b having one end coupled with the first shared linear portion B1 and the other end coupled with the third shared linear portion B3, a second bent linear portion 22b having one end coupled with the third shared linear portion B3 and the other end coupled with the second shared linear portion B2, a third bent linear portion 23b having one end coupled with the second shared linear portion B2 and the other end coupled with the fourth shared linear portion B4, and a fourth bent linear portion 24b having one end coupled with the fourth shared linear portion B4 and the other end coupled with the first shared linear portion B1.

The first bent linear portion 21b and the fourth bent linear portion 24b (constituting two bent linear portions out of the first to fourth bent linear portions) in the third wave-line annular body from one end of the stent 10 are formed to have the same number of bends (specifically two) and the same form/configuration at the time of inversion (inclusive of substantially the same form/configuration). In addition, although it is desirable that the first bent linear portion 21b and the fourth bent linear portion 24b have completely the same form/configuration at the time of inversion, they may have simply the same pattern as described above. Additionally, the second bent linear portion 22b and the third bent linear portion 23b (constituting the two other bent linear portions out of the first to fourth bent linear portions) are configured to have the same number of bends (specifically four) which is different from the number of bends of the above-mentioned two bent linear portions and have the same form at the time of inversion (inclusive of substantially the same as described above). In addition, although it is desirable that the second bent linear portion 22b and the third bent linear portion 23b have completely the same form at the time of inversion, they may have simply the same pattern as discussed above. The expression "at the time of inversion" refers to the time when up and down (in other words, top and bottom, or in other words, one end and the other end of the stent in the axial direction) are inverted in a state where the bent linear portions are shown in the drawings.

Even in the third wavy-line annular body from one end in the stent 10 of this embodiment, as shown in FIG. 8, two bent linear portions which have the same number of bends are also configured such that the directions of imaginary lines which connect one end and the other end of each bent linear portion are different from each other. Specifically, the direction of an imaginary line (a first imaginary line) M1 which connects one end and the other end of the first bent linear portion 21b, and the direction of an imaginary line (a fourth imaginary line) M4 which connects one end and the other end of the fourth bent linear portion 24b are different so as not to be parallel. Particularly, as shown in FIG. 8, it is preferable that the direction of the first imaginary line M1 and the direction of the fourth imaginary line M4 be different from each other, but the inclination angles of the imaginary lines to the central axis of the stent is the same (inclusive of substantially the same as described above). Similarly, the direction of an imaginary line (a second imaginary line) M2 which connects one end and the other end of the second bent linear portion 22b, and the direction of an imaginary line (a third imaginary line) M3 which connects one end and the other end of the third bent linear portion 23b are different so as not to be parallel. Particularly, as shown in FIG. 8, it is preferable that the direction of the second imaginary line M2 and the direction of the third imaginary line M3 be different from each other, but the inclination angles of the imaginary lines relative to the central axis of the stent is the same (inclusive of substantially the same as described above).

As shown in FIGS. 6 and 8, the even-numbered wave-line annular bodies from the one end of the stent 10 has the same form as the above-mentioned first pattern wavy-line annular body, and is shifted in the peripheral direction of the stent by several pitches (specifically, pitches equivalent to four other-end-side apexes or about 180 degrees with respect to the central axis of the stent). Additionally, the odd-numbered wave-line annular bodies from the one end of the stent 10 has the same form as the above-mentioned second pattern wavy-line annular body, and is shifted in the peripheral direction of the stent by several pitches (specifically, pitches equivalent to four one-end-side apexes or about 180□ with respect to the central axis of the stent).

In the stent 1, bent linear portions which have the same number of bends in the axial direction of the stent are arranged to line up in series. However, in the stent 10 of this embodiment, bent linear portions which have the same number of bends in the axial direction of the stent are arranged so they do not line up in series.

Specifically, as shown in FIG. 8, in the stent 10, a second wavy-line annular body from one end includes a bent linear portion [21a: pattern A; (A) in the drawing] having four bends, a bent linear portion [22a: pattern C; (C) in the drawing] having four bends and having a form which is vertically inverted from the bent linear portion of the pattern A, a bent linear portion [23a: pattern E; (E) in the drawing] having two bends, and a bent linear portion [24a: pattern G; (G) in the drawing] having two bends and having a form which is vertically inverted from the bent linear portion of the pattern E in this order in the peripheral direction.

In the wavy-line annular bodies excluding those at one end and the other end, substantially, a set composed of two bent linear portions having four bends and having different patterns, and a set composed of two bent linear portions having two bends and having different patterns are arranged in series from one end of the stent toward the base end side in the axial direction.

Specifically, the stent 10 has an axially continuous bent linear portion group starting from a bent linear portion [21a: pattern A; (A) in the drawing] having four bends. A bent linear portion [24b: pattern F; (F) in the drawing] having two bends is continuously arranged on the base end side of the pattern A in the axial direction, a bent linear portion [23a: pattern E; (E) in the drawing] having two bends is continuously arranged on the base end side of the bent linear portion of the pattern F in the axial direction, a bent linear portion [22b: pattern D; (D) in the drawing] having four bends is continuously arranged on the base end side of the bent linear portion of the pattern E in the axial direction, a bent linear portion (pattern A) having four bends is continuously arranged on the base end side of the bent linear portion of the pattern D in the axial direction, and the above-mentioned ones are repeated on the base end side of the bent linear portion of the pattern A in the axial direction, i.e., a bent linear portion (pattern F) having two bends is continuously arranged, a bent linear portion (pattern E) having two bends is continuously arranged on the base end side of the bent linear portion of the pattern F in the axial direction, a bent linear portion (pattern D) having four bends is continuously arranged on the base end side of the bent linear portion of the pattern E in the axial direction. The bent linear portion (pattern D) has a form in which the bent linear portion (pattern A) is inverted horizontally, and the bent linear portion (pattern F) has a form in which the bent linear portion (pattern E) is horizontally inverted. An imaginary line which connects one end and the other end of a bend of each of the bent linear portions (patterns A, F, E, D, A, F, E, and D) which are arranged substantially in series in the axial direction of the stent, as shown in FIG. 8 forms a zigzagging imaginary line on which peaks with different heights alternately appear.

Additionally, the stent 10 has an axially continuous bent linear portion group starting from a bent linear portion [22a: pattern C; (C) in the drawing] which has four bends. A bent linear portion [21b: pattern H; (H) in the drawing] having two bends is continuously arranged on the base end side of the bent linear portion (pattern C) in the axial direction, a bent linear portion [24a: pattern G; (G) in the drawing] having two bends is continuously arranged on the base end side of the bent linear portion of the pattern H in the axial direction, a bent linear portion [23b: pattern B; (B) in the drawing] having four bends is continuously arranged on the base end side of the bent linear portion of the pattern G in the axial direction, a bent linear portion (pattern C) having four bends is continuously arranged on the base end side of the bent linear portion of the pattern B in the axial direction, and the above-mentioned ones are repeated on the base end side of the bent linear portion of the pattern C in the axial direction, i.e., a bent linear portion (pattern H) having two bends is continuously arranged, a bent linear portion (pattern G) having two bends is continuously arranged on the base end side of the bent linear portion of the pattern H in the axial direction, a bent linear portion (pattern B) having four bends is continuously arranged on the base end side of the bent linear portion of the pattern G in the axial direction. The bent linear portion (pattern G) has a form in which the bent linear portion (pattern H) is horizontally inverted, and the bent linear portion (pattern C) has a form in which the bent linear portion (pattern B) is horizontally inverted. An imaginary line which connects one end and the other end of a bend of each of the bent linear portions (patterns C, H, G, B, C, H, G, and B) which are arranged substantially in series in the axial direction of the stent, as shown in FIG. 8, forms a zigzagging imaginary line on which peaks with different heights alternately appear. This zigzagging imaginary line is different from the zigzagging imaginary line formed by a bent linear portion group starting from the above-mentioned pattern A.

Moreover, the stent 10 has an axially continuous bent linear portion group starting from a bent linear portion (pattern E) having two bends. A bent linear portion (pattern D) having four bends is continuously arranged on the base end side of the bent linear portion (pattern E) in the axial direction, a bent linear portion (pattern A) having four bends is continuously arranged on the base end side of the bent linear portion of the pattern D in the axial direction, a bent linear portion (pattern F) having two bends is continuously arranged on the base end side of the bent linear portion of the pattern A in the axial direction, a bent linear portion (pattern E) having two bends is continuously arranged on the base end side of the bent linear portion of the pattern F in the axial direction, and the above-mentioned configuration is repeated on the base end side of the bent linear portion of the pattern E in the axial direction, i.e., a bent linear portion (pattern D) having four bends is continuously arranged, a bent linear portion (pattern A) having four bends is continuously arranged on the base end side of the bent linear portion of the pattern D in the axial direction, a bent linear portion (pattern F) having two bends is continuously arranged on the base end side of the bent linear portion of the pattern A in the axial direction. The bent linear portion (pattern F) has a form in which the bent linear portion (pattern E) is horizontally inverted, and the bent linear portion (pattern D) has a form in which the bent linear portion (pattern A) is horizontally inverted. An imaginary line which connects one end and the other end of a bend of each of the bent linear portions (patterns E, D, A, F, E, D, A, and F) which are arranged substantially in series in the axial direction of the stent, as shown in FIG. 8, forms a zigzagging imaginary line on which peaks with different heights alternately appear.

The stent 10 has an axially continuous bent linear portion group starting from a bent linear portion (pattern G) having two bends. A bent linear portion (pattern B) having four bends is continuously arranged on the base end side of the bent linear portion (pattern G) in the axial direction, a bent linear portion (pattern C) having four bends is continuously arranged on the base end side of the bent linear portion of the pattern B in the axial direction, a bent linear portion (pattern H) having two bends is continuously arranged on the base end side of the bent linear portion of the pattern C in the axial direction, a bent linear portion (pattern G) having two bends is continuously arranged on the base end side of the bent linear portion of the pattern H in the axial direction, and the above-mentioned ones are repeated on the base end side of the bent linear portion of the pattern G in the axial direction, i.e., a bent linear portion (pattern B) having four bends is continuously arranged, a bent linear portion (pattern C) having four bends is continuously arranged on the base end side of the bent linear portion of the pattern B in the axial direction, a bent linear portion (pattern H) having two bends is continuously arranged on the base end side of the bent linear portion of the pattern C in the axial direction. The bent linear portion (pattern H) has a form in which the bent linear portion (pattern G) is horizontally inverted, and the bent linear portion (pattern C) has a form in which the bent linear portion (pattern B) is horizontally inverted. An imaginary line which connects one end and the other end of a bend of each of the bent linear portions (patterns G, B, C, H, G, B, C, and H) which are arranged substantially in series in the axial direction of the stent forms a zigzagging imaginary line on which peaks with different heights alternately appear. This zigzagging imaginary line is different from the zigzagging imaginary line formed by a bent linear portion group starting from the above-mentioned pattern E.

Even in the stent 10 of this embodiment, a continuous imaginary line obtained by making a continuous imaginary line, which connects one end and the other end of each bent linear portion of the bent linear portions located substantially in series in the axial direction of the stent, is in the shape of a zigzag having apexes which project in the peripheral direction of the stent. Additionally, in this stent 10, the zigzagging continuous imaginary line is configured such that apexes which projects long in the peripheral direction of the stent and apexes which projects short in the peripheral direction of the stent alternate with each other.

The stent 10 of this embodiment has a more complicated configuration than the above-mentioned stent 1, and exhibits a more stable expansion retaining force at the time of expansion.

In addition, each shared linear portion has one apex itself of one-end-side or other-end-side bend in the wavy-line annular body 2 on one end side of the stent 10 in the axial direction as a starting end, and has a terminating end between apexes of one-end-side bend or other-end-side bend continuous with this apex (may be starting end). For example, a shared linear portion has a terminating end substantially near a midpoint between apexes of the one-end-side bend 2a continuous with the apex (also the starting end) of the bend 2b. In addition, although it is preferable that this terminating end be located at the midpoint, it may be located at a position which is anywhere between about 30/100 to about 49/100 of the total length between the apexes of the one-end-side bend 2a which are continuous with the apex (also the starting end of a shared linear portion) of the bend 2b. In addition, in this case, it is preferable that the position of this terminating end be shifted toward the apex of the one-end-side bend 2a away from the midpoint.

Since the stent 10 has the configuration as described above, it has a starting end branch formed by a starting end portion of a shared linear portion and a terminating end branch formed by a terminating end portion of the shared linear portion. Specifically, the starting end branch has a form which branches into two heading toward one end with the starting end as a branch point, and the terminating end branch has a form which branches into two heading toward the other end with the terminating end as a branch point.

Additionally, the stent 10 of this embodiment, as shown in FIGS. 6 and 8 and as described above, has a more complicated configuration than the above-mentioned stent 1, and has a homogeneous expansive force and the ability to change shape. The stent 10 also includes six shared linear portion group rows which extend substantially parallel to the central axis of the stent 10. The number of shared linear portions in each shared linear portion group row is 2 to 4, and the shared linear portions are more spread out than the stent 1.

Additionally, shared linear portions (for example, the first shared linear portion A1 and the second shared linear portion A2) located on one end side in one wavy-line annular body, and shared linear portions (for example, the third shared linear portion A3 and the fourth shared linear portion A4) located on the other end side extend in different directions with respect to the axis of the stent 10. Particularly, it is preferable that their directions be different from each other, but the inclination angles thereof to the central axis of the stent should be the same (inclusive of substantially the same as described above).

Additionally, as shown in FIGS. 6 and 8, an apex portion of the one-end-side bend 2a of the wavy-line annular body 2 enters into a space formed between apexes of the other-end-side bends 2b of one adjacent wavy-line annular body, and an apex portion of the other-end-side bend 2b of the wavy-line annular body 2 enters into a space between apexes of one-end-side bends 2a of the other adjacent wavy-line annular body.

Figure 7:
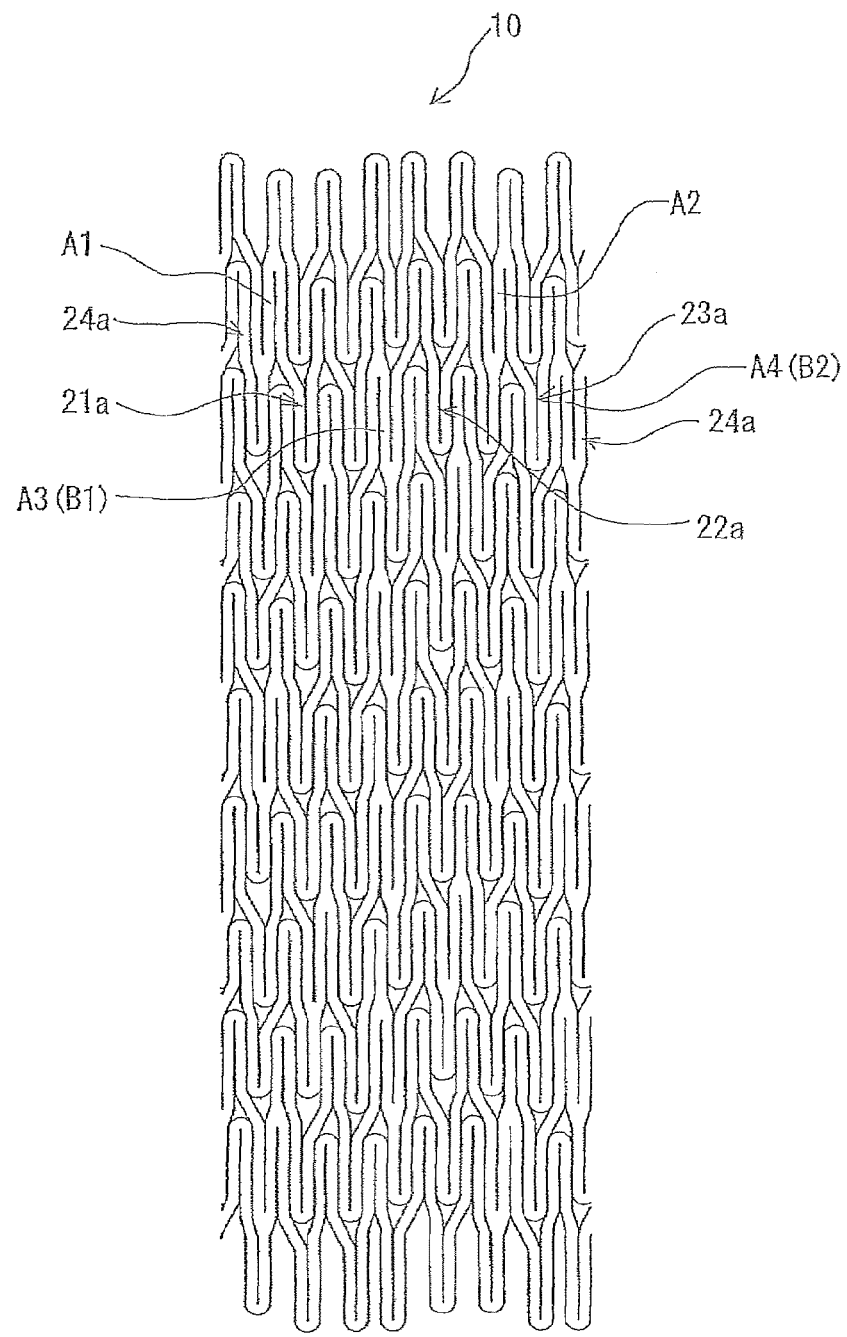
FIG. 7 is a development view of the stent shown in FIG. 5 in a state in which the diameter of the stent is reduced.

Moreover, in the stent 10 of this embodiment, in a contracted state shown in FIG. 7, there is almost no gap in the peripheral direction, and the respective elements are side by side. For this reason, a stable expansive force is exhibited at the time of expansion.

Additionally, similar to the stent 1 described above, in the stent 10 of this embodiment, as shown in FIG. 6, the wavy-line annular body 2 includes eight one-end-side apexes 2a, eight other-end-side apexes 2b, and sixteen substantially straight linear portions which connect them. Similarly, the wavy-line annular body adjacent to the wavy-line annular body 2 on the other end side in the axial direction includes eight one-end-side apexes 2a, eight other-end-side apexes 2b, and sixteen substantially straight linear portions which connect them. The above two wavy-line annular bodies 2 adjacent to each other are integrated by providing two common linear portions. Additionally, the above two wavy-line annular bodies 2 adjacent to each other are configured to overlap each other by about ½ of the axial length of one wavy-line annular body (in other words, so as to shift toward the other end). For this reason, one-end-side apex 2a of a wavy-line annular body on the other end side is positioned so it enters the space between the other-end-side apexes of a wavy-line annular body on one end side (the one-end-side apex 2a of a wavy-line annular body on the other end side is positioned so it extends beyond a line connecting the other-end-side apexes of a wavy-line annular body on one end side). The first shared linear portion A1 is a substantially straight portion which couples the other-end-side apex 2b (A1a) of the wavy-line annular body 2 on one end side with the one-end-side apex 2a (A1b) of the wavy-line annular body 2 on the other end side. Additionally, the second shared linear portion A2 is a substantially straight portion which couples the other-end-side apex 2b (A2a) of the wavy-line annular body 2 on one end side with the one-end-side apex 2a (A2b) of the wavy-line annular body 2 on the other end side. An apex shared by a shared linear portion loses the form of the apex serving as a free end, and constitutes a branch.

Similarly, the wavy-line annular body 2 adjacent to the above wavy-line annular body on the other side in the axial direction is also integrated by providing two common linear portions. These two wavy-line annular bodies 2 adjacent to each other are also configured so as to overlap each other by about ½ of the axial length of one wavy-line annular body (in other words, so as to shift toward the other end). For this reason, one-end-side apex 2a of a wavy-line annular body on the other end side is positioned so it enters into the space between the other-end-side apexes of a wavy-line annular body on one end side. The first shared linear portion B1 (A3) is a substantially straight portion which couples the other-end-side apex 2b (A3b) of the wavy-line annular body 2 on one end side with the one-end-side apex 2a (A3a) of the wavy-line annular body 2 on the other end side. Additionally, the second shared linear portion B2 (A4) is also a substantially straight portion which couples the other-end-side apex 2b (A4b) of the wavy-line annular body 2 on one end side with the one-end-side apex 2a (A4a) of the wavy-line annular body 2 on the other end side. An apex shared by a shared linear portion loses the form of the apex serving as a free end, and constitutes a branch.

FIG. 6 illustrates the following features of the stent other than the common or shared linear portions in the stent 10. In a wavy-line annular body, the first bent linear portion 21a having the terminating end A1b (midpoint) of the first shared linear portion A1 as a starting point extends diagonally toward the other end and is bent at the first other-end-side apex 2b, extends diagonally toward one end and is bent at the first one-end-side apex 2a, extends again diagonally toward the other end and is bent at the second other-end-side apexes 2b, extends again diagonally toward one end and is bent at the second one-end-side apex 2a, and has the midpoint A3a (also the starting point of the third shared linear portion A3) between the second one-end-side apex and the next other-end-side apex as a terminating point. Additionally, the second bent linear portion 22a having the terminating end A3b (midpoint) of the third shared linear portion A3 as a starting point extends diagonally toward one end and is bent at the first one-end-side apex 2a, extends diagonally toward the other end and is bent at the first other-end-side apex 2b, extends again diagonally toward one end and is bent at the second one-end-side apex 2a, extends again diagonally toward the other end and is bent at the second other-end-side apex 2b, and has the midpoint A2a (also the starting point of the second shared linear portion A2) between this second other-end-side apex and the next one-end-side apex as a terminating point. Additionally, in a wavy-line annular body, the third bent linear portion 23a having the terminating end A2b (midpoint) of the second shared linear portion A2 as a starting point extends diagonally toward the other end and is bent at the first other-end-side apex 2b, extends diagonally toward one end and is bent at the first one-end-side apex 2a, and has the midpoint A4a (also the starting point of the fourth shared linear portion A4) between the first one-end-side apex and the next other-end-side apex as a terminating point. Additionally, the fourth bent linear portion 24a having the terminating end A4b (midpoint) of the fourth shared linear portion A4 as a starting point extends diagonally toward one end and is bent at the first one-end-side apex 2a, extends diagonally toward the other end and is bent at the first other-end-side apex 2b, and has the midpoint A1a (also the starting point of the first shared linear portion A1) between the first other-end-side apex and the next one-end-side apex as a terminating point.

Consequently, in all the first to fourth bent linear portions 21*a*, 22*a*, 23*a*, and 24*a*, both the starting point and the terminating point are located at a midpoint of a straight portion which connects the two apexes. In other words, all the first to fourth bent linear portions connect the midpoints of a straight portion which connects the two apexes.

Additionally, the first shared linear portion A1 and third shared linear portion A3 which are in the state of being connected together by the first bent linear portion face different directions with respect to the central axis of the stent. Similarly, the second shared linear portion A2 and fourth shared linear portion A4 which are in the state of being connected together by the third bent linear portion face different directions with respect to the central axis of the stent. Additionally, the first shared linear portion A1 and second shared linear portion A2 incline in the same direction with respect to the central axis of the stent. The third shared linear portion A3 and fourth shared linear portion A4 incline in the same direction with respect to the central axis of the stent. The first shared linear portion A1 and the third shared linear portion A3 incline in different directions with respect to the central axis of the stent and the second shared linear portion A2 and the fourth shared linear portion A4 incline in different directions with respect to the central axis of the stent.

In the stents of all the embodiments described above, generally, the external diameter at the time of expansion (at the time of no diameter reduction or at the time of restoration) is 2.0 to 30 mm, and preferably 2.5 to 20 mm, the wall thickness is 0.04 to 1.0 mm, and preferably 0.06 to 0.5 mm, and the length is 10 to 150 mm, and more preferably 15 to 100 mm, although they change depending on parts for indwelling. Particularly, in the case of an indwelling vascular stent, its external diameter (at the time of no diameter reduction or at the time of restoration) is 2.0 to 14 mm, and preferably 2.5 to 12 mm, its wall thickness is 0.04 to 0.3 mm, and preferably 0.06 to 0.22 mm, and its length is 5 to 100 mm, and more preferably 10 to 80 mm.

The stents of all the embodiments described above are integrally formed in a substantially cylindrical shape, by removing parts of a metallic pipe, which can give superelastic characteristics, except those linear portions which constitute a stent.

Metals which can be used to impart superelastic characteristics include so-called superelastic alloys which are suitable for use here. Particularly preferably, superelastic metal bodies, such as a TiNi alloy of Ni of 49 to 54 atomic %, a Cu—Zn alloy of Zn of 38.5 to 41.5 weight %, a Cu—Zn—X alloy (X=Be, Si, Sn, Al, Ga) of X of 1 to 10 weight %, and an Ni—Al alloy of Al of 36 to 38 atomic %, are used suitably. The above TiNi alloy is particularly preferable. Additionally, mechanical properties can be changed suitably by using a Ti—Ni—X alloy (X=Co, Fe, Mn, Cr, V, Al, Nb, W, B, Au, Pd, etc.) obtained by substituting a portion of a Ti—Ni alloy with an X of 0.01 to 10.0%, or by using a Ti—Ni—X alloy (X=Cu, Pb, Zr) obtained by substituting a portion of a Ti—Ni alloy with an atom of 0.01 to 30.0% and selecting the rate of cold working, or/and the conditions of final heat treatment.

Additionally, mechanical properties can be changed suitably by selecting the rate of cold working, and/or the conditions of final heat treatment by using the above Ti—Ni—X alloy. The buckling strength (yield stress when loading at the time of development of superelastic characteristics) of the superelastic alloys to be used is 5 to 200 kgf/mm$^2$ (22° C.), and more preferably 8 to 150 kgf/mm$^2$, and the restoration stress (yield stress when unloading) thereof is 3 to 180 kgf/mm$^2$ (22° C.), are more preferably 5 to 130 kgf/mm$^2$. The term superelastic means the recovering of their substantial original shape without requiring heating after the release of load even if normal metal is deformed (bent, pulled, compressed) to a region where it deforms like plastic at service temperature.

The stent is manufactured by removing (for example, cutting or melting) the stent non-components by using a metallic pipe which can give the above superelastic characteristics, and thereby, is made into an integrally formed object. In addition, the superelastic metallic pipe used for formation of the stent disclosed here can be manufactured by the melting in an inert gas or vacuum atmosphere to form an ingot of an superelastic alloy, such as a Ti—Ni alloy, polishing this ingot mechanically, then performing hot pressing and extrusion to form a large-diameter pipe, then repeating a dies-drawing process and a heat treatment process sequentially to thereby form a small-diameter pipe of predetermined wall thickness and external diameter, and finally polishing the surface of the pipe chemically or physically. The formation of a stent base by this superelastic metallic pipe can be performed by cutting (for example, mechanical polishing, laser cutting), electric discharge machining, chemical etching, etc., and can be performed by combination use of them.

By performing suitable heat treatment on the stent formed as described above, the stent demonstrates superelastic characteristics both before and after insertion into a living body.

Additionally, it is preferable that the self-expandable stents of all the embodiments described above be integrally formed in a substantially cylindrical shape, by removing portions other that those parts constituting the linear portions of the stent, from a metallic pipe which can give superelastic characteristics. It is preferable that the stents show superelastic characteristics both before and after insertion into a living body. Moreover, it is preferable that the line width of each of the linear portions of the stents be 80 to 170 μm, and, the thickness of the linear portion be 180 to 230 μm.

Moreover, in the stents, it is preferable that the compressive load for compressing the axial length of the stents by 20% be 10 to 20 gf. In other words, in the stents disclosed here, it is preferable that the stents can be compressed by 20% in the axial direction by a compressive load of 10 to 20 gf.

In addition, in the stents disclosed here, it is preferable that the stents can be compressed by 20% in the axial direction by a compressive load of 12 to 14 gf. Additionally, in the stent disclosed here, it is preferable that the stent can be compressed by 20% or more in the axial direction by a compressive load of 10 to 20 gf.

Additionally, a biocompatible material may be coated on an inner surface, an outer surface or both surfaces of the stents. As the biocompatibible material, synthetic resin or metal which has biocompatibility are available. Gold plating using an electroplating method, stainless steel plating using a vacuum deposition method, silicon carbide, diamond-like carbon, or titanium nitride plating or gold plating, using a sputtering method, and the like are available as a method for covering the surface of a stent with inert metal. Additionally, although the synthetic resin can be selected from a thermoplastic resin or a thermosetting resin, for example, polyolefine (for example, polyethylene, polypropylene, ethylene propylene copolymer, and the like), polyvinyl chloride, ethylene-vinyl acetate copolymer, polyamide elastomer, polyurethane, polyester, fluororesin, silicone resin, and the like can be used, and preferably, polyolefine, polyamide elastomer, polyester or polyurethane, silicone resin, and biodegradable resin (for example, polylactic acid, polyglycolic acid, and copolymer of both) can be used. It is preferable that a synthetic resin film be pliable such that it does not hinder the curving of a frame which constitutes a stent. The wall thickness of the synthetic resin film is 3 to 300 μm, and preferably 5 to 100 μm.

As methods for of thinly coating synthetic resin on the surface of a stent, for example, there is a method of inserting a stent into synthetic resin which is in a molten state or a solution state to coat the stent, a chemical vapor deposition method of coating a stent while a monomer is polymerized on the surface of a superelastic metallic pipe, and the like. In a case where ultra-thin resin coating is required, coating using a dilute solution or chemical vapor deposition is suitable. Additionally, in order to further improve a biocompatibible material, an antithrombotic material may be coated on or fixed to the above resin film. Although various kinds of well-known resins can be used independently or by mixture used as an antithrombotic material, for example, polyhydroxy ethyl methacrylate, a copolymer of hydroxy ethyl methacrylate and styrene (for example, HEMA-St-HEMA block copolymer) and the like can be suitable for use.

EXAMPLES

Next, an example of a stent constructed according to the disclosure here will be described.

Example 1

An alloy pipe made of a TiNi alloy (Ni of 51 atomic %) was cold-worked, and a metallic pipe with the external diameter of about 1.9 mm, a wall thickness of 0.25 mm, and a length of about 100 mm was manufactured. Then, the metallic pipe was set on a jig with a rotary motor to which a fastener mechanism is attached so that an axis does not deviate, and this was set on an X table (longitudinal axis of the stent production device) which can be controlled numerically. The X table and the rotary motor were connected to a personal computer, and the output of the personal computer was input to a numerical controller of the X table and the rotary motor. Drawing software was stored in the personal computer, and a development view of a stent having a construction as shown in FIG. 3 was input. By using such a configuration, the X table and the rotary motor are driven on the basis of the drawing information output from the personal computer.

By irradiating a metallic pipe with a laser beam in this way, a stent base of a shape having a development view like FIG. 3 was manufactured.

As laser beam machining conditions of the above metallic pipe, machining was performed at an average output of 5.5 W and at a driving speed of 180 mm/min. Then, internal surface grinding was performed on the above stent base.

Next, burrs created on the inner surface of the stent base were removed by an elongate file, the stent base was fitted onto a 2 mm rod with a taper, and the diameter of the stent was increased. In this state, the stent base was put into an electric furnace of 450 to 550° C., and was taken out and quenched after a certain period of time. Next, the stent base was fitted onto a 4 mm rod with a taper, and the same operation was performed. Next, expansion working of the stent base was performed by 6 mm and finally 8 mm rods with a taper, and the expanded stent base with an internal diameter of 8 mm was obtained. The surface polishing (specifically, chemical polishing) of the expanded stent base was performed to obtain the stent shown in FIG. 1. In the stent manufactured in this way, its external diameter was about 8 mm, its total length was about 45 mm, the width of each linear portion was 0.11 mm to 0.12 mm, its wall thickness was 0.19 mm to 0.2 mm, the axial length of an annular body was about 3 mm, and the length of a shared linear portion was about 1.6 mm. This stent included a sufficient expansive force, was pliable even if it was bent in any direction, and it did not exhibit characteristics such that it was pliable in a certain direction but less pliable in other directions.

Example 2

The same operation as Example 1 was performed except that a development view of a stent of the construction shown in FIG. 7 was input to the personal computer, and a stent base was manufactured as shown in FIG. 5. Also, the stent base formed similar to Example 1 was processed, and the stent was manufactured which has the configuration as shown in FIG. 5. In the stent manufactured in this way, its external diameter was about 8 mm, its total length was about 45 mm, the width of each linear portion was 0.11 mm to 0.12 mm, its wall thickness was 0.19 mm to 0.2 mm, the axial length of an annular body was about 3 mm, and the length of a shared linear portion was about 1.6 mm. This stent included a sufficient expansive force, was pliable even if it was bent in any direction, and it did not exhibit characteristics in which it was pliable in a certain direction but less pliable in other directions.

The self-expandable stent disclosed here includes a number of features and aspects.

The self-expandable stent includes a plurality of wavy-line annular bodies in the axial direction, wherein each wavy-line annular body has a plurality of one-end-side bends having apexes on one end side of the stent in the axial direction and a plurality of other-end-side bends having apexes on the other end side of the stent in the axial direction. The wavy-line annular bodies adjacent to each other on the other end side of the stent in the axial direction have at least two shared linear portions having a starting end at one apex or in its vicinity of the other-end-side bend in the wavy-line annular body on one end side of the stent in the axial direction and having a terminating end at a substantially intermediate portion between the apex of the other-end-side bend and the apex of the one-end-side bend. The adjacent wavy-line annular bodies are integrated by the shared linear portions, wherein each wavy-line annular body of the stent other than at least those at one end and a base end has a first shared linear portion and a second shared linear portion located on one axial end side, a third shared linear portion and a fourth shared linear portion located on the other axial end side. In addition, each wavy-line annular body of the stent other than at least those at one end and a base end includes a first bent linear portion having one end coupled with the first shared linear portion and the other end coupled with the third shared linear portion, a second bent linear portion having one end coupled with the third shared linear portion and the other end coupled with the second shared linear portion, a third bent linear portion having one end coupled with the second shared linear portion and the other end coupled with the fourth shared linear portion, and a fourth bent linear portion having one end coupled with the fourth shared linear portion and the other end coupled with the first shared linear portion. Two bent linear portions out of the first to fourth bent linear portions have the same number of bends and the same form at the time of inversion, and the other two bent linear portions out of the first to fourth bent linear portions have the same number of bends which is different from the number of bends of the two bent linear portions and the same form at the time of inversion.

For this reason, since an expansive force is not substantially developed, a connecting portion which may exert influence the time of curving of a stent is not provided, and the adjacent wavy-line annular bodies are integrated by a shared linear portion, the stent has a sufficient expansive force, and an expansive force which is uniform as a whole. Moreover, since the forms of the first to the fourth bent linear portion are configured as described, the whole stent has good coverage at the time of expansion, and has an expansive force above a certain level, and is pliable in the axial direction.

The stent also embodies other aspects and features.

For example, two bent linear portions having the same number of bends in the one wavy-line annular body are configured such that the directions of imaginary lines which connect one end and the other end of each bent linear portion are different from each other.

The number of bends in two bent linear portions with more bends of the first to fourth bent linear portions is 4 to 8, and the number of bends in two bent linear portions with fewer bends out of the first to fourth bent linear portions is 2 to 4.

The number of bends in two bent linear portions with more bends of the first to fourth bent linear portions is 4, and the number of bends in two bent linear portions with fewer bends out of the first to fourth bent linear portions is 2.

The stent has a starting end branch formed at the starting end of the shared linear portion, and a terminating end branch formed at the terminating end of the shared linear portion.

An apex of the one-end-side bend of the wavy-line annular body enters into a space formed between the other-end-side bends of one adjacent wavy-line annular body, and an apex of the other-end-side bend of the wavy-line annular body enters into a space between one-end-side bends of the other adjacent wavy-line annular body.

The self-expandable stent is configured so that a continuous imaginary line, obtained by making a continuous imaginary line which connects one end and the other end of each bent linear portion of the bent linear portions located substantially in series in the axial direction of the stent, is in the shape of a zigzag having apexes which project in the peripheral direction of the stent.

According to one aspect, the zigzagging continuous imaginary line has a plurality of apexes which project by almost the same length in the peripheral direction of the stent. According to another aspect, the zigzagging continuous imaginary line is configured such that apexes which project long in the peripheral direction of the stent and apexes which project short in the peripheral direction of the stent alternate with each other.

The detailed description above describes preferred embodiments of the stent disclosed here with reference to the accompanying drawings. However, it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

The invention claimed is:

1. A self-expandable stent comprising:

a plurality of wavy-line annular bodies arranged in an axial direction, each wavy-annular body possessing one end side and an other-end-side, the one-end-side being located on one axial end of the wavy-line annular body and the other-end-side being located on an opposite axial end of the wavy-line annular body;

each of said plurality of wavy-line annular bodies comprising a plurality of one-end-side bends each possessing an apex positioned on the one end side and a plurality of other-end-side bends each having an apex positioned on the other end side;

the wavy-line annular bodies comprising a first wavy-line annular body, a second wavy-line annular body, and a third wavy-line annular body;

the first and second wavy-line annular bodies being positioned axially adjacent one another with no other wavy-line annular body positioned axially between the first and second wavy-line annular bodies;

the second and third wavy-line annular bodies being positioned axially adjacent one another with no other wavy-line annular body positioned axially between the second and third wavy-line annular bodies;

the first and second wavy-line annular bodies comprising first and second shared linear portions each having a starting end at one of the apexes on the other-end-side of the first wavy-line annular body and a terminating end located at an intermediate position between said one apex on the other-end-side of the first wavy-line annular body and one of the apexes on the one-end side of the first wavy-line annular body and at the one of the apexes on the second wavy-line annular body, the first and second shared linear portions being integral and unitarily formed with both the first and second wavy-line annular bodies to connect together the first and second wavy-line annular bodies;

the second and third wavy-line annular bodies comprising third and fourth shared linear portions each having a starting end at one of the apexes on the other-end-side of the second wavy-line annular body and a terminating end located at an intermediate position between said one apex on the other-end-side of the second wavy-line annular body and one of the apexes on the one-end-side of the second wavy-line annular body and at one of the apexes on the third wavy-line annular body, the third and fourth shared linear portions being integral and unitarily formed with both the second and third wavy-line annular bodies to connect together the second and third wavy-line annular bodies;

each of the first, second and third wavy-line annular bodies comprising a first bent linear portion, a second bent linear portion, a third bent linear portion and a fourth bent linear portion;

each of the first to fourth bent linear portions comprising at least two bends including the apex;

the first bent linear portion of the second wavy-line annular body possessing one end in direct contact with the first shared linear portion and the other end in direct contact with the third shared linear portion, the second bent linear portion of the second wavy-line annular body possessing one end in direct contact with the third shared linear portion and the other end in direct contact with the second shared linear portion, the third bent linear portion of the second wavy-line annular body possessing one end in direct contact with the second shared linear portion and the other end in direct contact with the fourth shared linear portion, and the fourth bent linear portion of the second wavy-line annular body possessing one end in direct contact with the fourth shared linear portion and the other end in direct contact with the first shared linear portion; and a first pair of the bent linear portions out of the first to fourth bent linear portions possessing a first equal number of bends including the apex, a configuration of each one of the first pair being defined such that, upon inversion, one of the first pair of the bent linear portions possesses a configuration that is the same as the other one of said first pair of the bent linear portions prior to inversion, and a second pair of the bent linear portions out of the first to fourth bent linear portions possessing a second equal number of bends including the apex which is different from the first equal number of bends, a configuration of each one of the second pair being defined such that, upon inversion, one of the second pair of the bent linear portions possesses a configuration that is the same as the other one of said second pair of the bent linear portions prior to inversion.

2. The self-expandable stent according to claim 1, wherein the first pair of bent linear portions possessing the first equal number of bends comprise first and second bent linear portions, and further comprising a first imaginary line connecting the one end and the other end of the first bent linear portion, and a second imaginary line connecting the one end and the other end of the second bent linear portion, the first and second imaginary lines being non-parallel to each other.

3. The self-expandable stent according to claim 1, wherein the number of bends in one of the first and second pair of bent linear portions possessing more bends is 4 to 8, and the number of bends in the other of the first and second pair of bent linear portions possessing fewer bends is 2 to 4.

4. The self-expandable stent according to claim 1, wherein the first and second wavy-line annular bodies are connected to one another only by the first and second shared linear portions, and the second and third of wavy-line annular bodies are connected to one another only by the third and fourth shared linear portions.

5. The self-expandable stent according to claim 1, wherein the number of bends in one of the first and second pair of bent linear portions possessing more bends is 4, and the number of bends in the other of the first and second pair of bent linear portions possessing fewer bends is 2.

6. The self-expandable stent according to claim 1, wherein the stent comprises a starting end branch formed at the starting end of the first and second shared linear portions, and a terminating end branch formed at the terminating end of the third and fourth shared linear portions.

7. The self-expandable stent according to claim 1, wherein the apex of each of the one-end-side bends of the second wavy-line annular body enters into a space formed between the other-end-side bends of the first wavy-line annular body so that the apex of each of the one-end-side bends of the second wavy-line annular body extends beyond a line connecting the apexes of the other-end-side bends of the first wavy-line annular body that are circumferentially adjacent each other.

8. The self-expandable stent according to claim 1, wherein a continuous imaginary line which connects one end and the other end of each of the bent linear portions that are located in series in the axial direction possesses a zigzag shape having apexes which project in a peripheral direction of the stent.

9. The self-expandable stent according to claim 8, wherein the zigzagging continuous imaginary line has a plurality of apexes which project by a common length in the peripheral direction of the stent.

10. The self-expandable stent according to claim 8, wherein the zigzagging continuous imaginary line is configured such that some apexes project relatively longer in the peripheral direction of the stent and some apexes project relatively shorter in the peripheral direction of the stent, the zigzagging continuous imaginary line being configured such that the apexes projecting relatively longer in the peripheral direction and the apexes projecting relatively shorter in the peripheral direction alternate with each other.

11. The self-expandable stent according to claim 1, wherein the first and second shared linear portions extend in the same direction with respect to the axis of the stent, the third and fourth shared linear portions extend in the same direction with respect to the axis of the stent, and the direction of the first and second shared linear portions and the direction of the third and fourth shared linear portions is different from each other.

12. The self-expandable stent according to claim 11, wherein an inclination angle of each of the shared linear portions relative to the central axis of the stent is the same.

13. The self-expandable stent according to claim 1, wherein the first pair of bent linear portions possessing the first equal number of bends including the apex comprise first and second bent linear portions, and further comprising a first imaginary line connecting the one end and the other end of the first bent linear portion, and a second imaginary line connecting the one end and the other end of the second bent linear portion, the first and second imaginary lines being non-parallel to each other, and the number of bends including the apex in one of the first and second pair of bent linear portions possessing more bends is four, and the number of bends including the apex in the other of the first and second pair of bent linear portions possessing fewer bends is two.

* * * * *